United States Patent
Volckens et al.

(10) Patent No.: US 9,482,620 B2
(45) Date of Patent: Nov. 1, 2016

(54) PORTABLE PARTICLE SPECTROMETER

(71) Applicant: Colorado State University Research Foundation, Fort Collins, CO (US)

(72) Inventors: John Volckens, Fort Collins, CO (US); Kimberly Anderson, Fort Collins, CO (US); David Leith, Chapel Hill, NC (US); Mwangi T. Ndonga, Broomfield, CO (US); Azer Yalin, Fort Collins, CO (US); Christopher M. Limbach, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 14/918,798

(22) Filed: Oct. 21, 2015

(65) Prior Publication Data
US 2016/0109349 A1    Apr. 21, 2016

Related U.S. Application Data

(60) Provisional application No. 62/066,644, filed on Oct. 21, 2014.

(51) Int. Cl.
| | | |
|---|---|---|
| G01N 21/00 | (2006.01) | |
| G01N 21/71 | (2006.01) | |
| G01J 3/443 | (2006.01) | |
| G01N 1/22 | (2006.01) | |
| G01N 15/10 | (2006.01) | |
| G01N 15/00 | (2006.01) | |

(52) U.S. Cl.
CPC .............. *G01N 21/718* (2013.01); *G01J 3/443* (2013.01); *G01N 1/2202* (2013.01); *G01N 15/10* (2013.01); *G01N 2001/2223* (2013.01); *G01N 2015/0046* (2013.01)

(58) Field of Classification Search
CPC .............. G01J 3/02; G01J 3/513; G01J 3/51; G01N 15/1459; G01N 21/65
USPC .......................................................... 356/73
See application file for complete search history.

(56) References Cited

U.S. PATENT DOCUMENTS

| | | | |
|---|---|---|---|
| 3,312,342 A | 4/1967 | Brown | |
| 3,550,773 A | 12/1970 | Villani et al. | |
| 4,301,002 A | 11/1981 | Loo | |
| 4,473,296 A | 9/1984 | Shofner et al. | |
| 4,640,768 A | 2/1987 | Morbioli et al. | |
| 4,689,052 A | 8/1987 | Ogren et al. | |
| 4,837,442 A * | 6/1989 | Manglos ................. | G01T 3/001 250/390.01 |
| 4,902,318 A | 2/1990 | Stevens et al. | |

(Continued)

OTHER PUBLICATIONS

Gibson et al. "A Personal Inspirable Aerosol Spectrometer for Applications in Occupational Hygiene Research." Annals of Occupational Health. vol. 31, No. 4A. pp. 463-479. 1987.

(Continued)

*Primary Examiner* — Tarifur Chowdhury
*Assistant Examiner* — Md M Rahman
(74) *Attorney, Agent, or Firm* — Faegre Baker Daniels LLP

(57) ABSTRACT

Methods and systems for characterizing particles in an aerosol are disclosed. A system includes a collection container that utilizes the principles of elutriation to collect particles of selected aerodynamic diameter ranges within a measurement region. A particle detector is used to detect and characterize particles that have settled into the measurement region.

12 Claims, 10 Drawing Sheets

(56) References Cited

U.S. PATENT DOCUMENTS

| | | | |
|---|---|---|---|
| 5,372,718 A * | 12/1994 | Zebian | B01D 29/117 210/301 |
| 5,571,945 A | 11/1996 | Koutrakis et al. | |
| 6,238,579 B1 * | 5/2001 | Paxton | B01D 21/2411 209/715 |
| 6,320,663 B1 * | 11/2001 | Ershov | G01J 1/4257 356/454 |
| 6,435,043 B1 | 8/2002 | Ferguson et al. | |
| 7,201,879 B2 | 4/2007 | Hill et al. | |
| 7,591,980 B2 | 9/2009 | Call et al. | |
| 8,539,840 B2 | 9/2013 | Ariessohn et al. | |
| 8,561,486 B2 | 10/2013 | Novosselov et al. | |
| 2004/0006953 A1 * | 1/2004 | Carroll | B01D 50/002 55/337 |
| 2004/0056188 A1 * | 3/2004 | Reents, Jr. | H01J 49/40 250/287 |
| 2007/0046934 A1 | 3/2007 | Roy | |
| 2008/0196514 A1 | 8/2008 | Kenny | |
| 2010/0208260 A1 * | 8/2010 | Carr | G01N 21/643 356/326 |
| 2011/0203931 A1 | 8/2011 | Novosselov et al. | |
| 2012/0311811 A1 * | 12/2012 | Hollis | A47L 7/0023 15/327.1 |
| 2013/0341275 A1 * | 12/2013 | Kusters | A61M 1/0272 210/650 |
| 2014/0247450 A1 | 9/2014 | Han | |
| 2014/0354976 A1 | 12/2014 | Evenstad et al. | |

OTHER PUBLICATIONS

Lidén et al. "Workplace Validation of a Laboratory Evaluation Test of Samplers for Inhalable and "Total" Dust." Journal of Aerosol Science. vol. 31, No. 2. pp. 199-219. 2000.

Mark et al. "A New Personal Sampler for Airborne Total Dust in Workplaces." Annals of Occupational Hygiene. vol. 30, No. 1. pp. 89-102. 1986.

Soderholm, Sidney C. "Proposed International Conventions for Particle Size-Selective Sampling". Annals of Occupational Hygiene. vol. 33, No. 3. pp. 301-320.

International Application No. PCT/US2015/056666. Notification of Transmittal of the International Search Report and the Written Opinion of the International Searching Authority, or the Declaration. 9 pages. International Filing Date: Oct. 21, 2015. Mail Date: Jan. 11, 2016.

Andersen et al. "Nasal cancers, symptoms and upper airway function in woodworkers." British journal of industrial medicine. 34:201-207. 1977.

Armendariz et al. "Concentration measurement and counting efficiency for the aerodynamic particle sizer 3320." Journal of Aerosol Science. 33:133-148. 2002.

Baan et al. "A review of human carcinogens—Part F: chemical agents and related occupations." The lancet oncology. 10:1143-1144. 2009.

Baldwin et al. "A survey of wind speeds in indoor workplaces." Annals of Occupational Hygiene. 42:303-313. 1998.

Baron, P. A. "Calibration and use of the aerodynamic particle sizer (APS 3300)." Aerosol Science and Technology. 5:55-67. 1986.

Bonneterre et al. "Sino-nasal cancer and exposure to leather dust." Occupational Medicine. 57:438-443. Jun. 2007.

Bush et al. Laboratory animal allergy. Journal of allergy and clinical immunology. 102:99-112. 1998.

Chen et al. "Performance of a TSI aerodynamic particle sizer." Aerosol science and technology. 4:89-97.1985.

Cheng et al. "Particle deposition in a cast of human oral airways." Aerosol Science & Technology. 31:286-300. 1999.

El Ghissassi et al. "A review of human carcinogens—part D: radiation." The lancet oncology. 10:751-752. Aug. 2009.

El Karim et al. "Respiratory and allergic disorders in workers exposed to grain and flour dusts." Archives of Environmental Health: An International Journal. 41:297-301. Sep./Oct. 1986.

Fargie et al. "Developing laminar flow in a pipe of circular cross-section." Proceedings of the Royal Society of London. A. Mathematical and Physical Sciences. 321:461-476. 1971.

Görner et al. "Laboratory Study of Selected Personal Inhalable Aerosol Samplers." Annals of Occupational Hygiene 54:165-187. 2010.

Grinshpun et al. "Development and evaluation of an aerosol monitor with low wind sensitivity and uniform filter leposition." Journal of Aerosol Science. 26:S187-S188. 1995.

Kalatoor et al. "New aerosol sampler with low wind sensitivity and good filter collection uniformity." Atmospheric Environment. 29:1105-1112. 1995.

Kanerva et al. "Occupational allergic rhinitis in Finland." International archives of occupational and environmental health. 64:565-568. 1993.

Kenny et al. "The sampling efficiency of personal inhalable aerosol samplers in low air movement environments." Journal of aerosol science. 30:627-638. 1999.

Kenny et al. "A collaborative European study of personal inhalable aerosol sampler performance." The Annals of occupational hygiene. 41:135-153. 1997.

Labus et al. (1972). "Experimental investigation of an axisymmetric free jet with an initially uniform velocity profile." National Aeronautics and Space Administration. May 1972.

Lidén et al. "Workplace validation of a laboratory evaluation test of samplers for inhalable and "total" dust." Journal of aerosol science. 31:199-219. 2000.

Luce et al. "Sinonasal cancer and occupational exposure to textile dust" American journal of industrial medicine. 32:205-210. 1997.

Marshall et al. "The behaviour of regular-shaped non-spherical particles in a TSI aerodynamic particle sizer." Journal of Aerosol Science. 22:73-89. 1991.

McNaughton et al. "Submerged jets in short cylindrical flow vessels." Journal of Fluid Mechanics. 25:367-375. 1966.

Moscato et al. "Occupational rhinitis." Allergy 63:969-980. 2008.

O'Shaughnessy, P. T. and Raabe, O. G. (2003). A comparison of cascade impactor data reduction methods. Aerosol Science & Technology 37:187-200.

Pesch et al. "Occupational risks for adenocarcinoma of the nasal cavity and paranasal sinuses in the German wood Industry." Occupational and environmental medicine. 65:191-196. 2008.

Peters et al. "Comparison of the Grimm 1.108 and 1.109 portable aerosol spectrometer to the TSI 3321 aerodynamic particle sizer for dry particles." Annals of Occupational Hygiene. 50:843-850. 2006.

Ferreira et al. "ImageJ User Guide ImageJ / Fiji 1.46r." National Institute of Health. 198 pages. 2012.

Reynolds, A. J. "Observations of a liquid-into-liquid jet. Journal of Fluid Mechanics" 14:552-556. 1962.

Rushton et al. "Occupational cancer burden in Great Britain." British journal of cancer. 107:S3-S7. 2012.

Slager et al. "Rhinitis associated with pesticide exposure among commercial pesticide applicators in the Agricultural Health Study." Occupational and environmental medicine. 66:718-724.2009.

Slovak et al. "Laboratory animal allergy: a clinical survey of an exposed population." British journal of industrial medicine. 38:38-41. Feb. 1981.

Spear et al. "Assessment of Particle Size Distributions of Health-relevant Aerosol Exposures of Primary Lead Smelter Workers." Annals of Occupational Hygiene 42:73-80. 1998.

Straif et al. "A review of human carcinogens—part C: metals, arsenic, dusts, and fibres." The lancet oncology. 10:453-454. 2009.

Volckens et al. "Counting and particle transmission efficiency of the aerodynamic particle sizer." Journal of Aerosol Science. 36:1400-1408. 2005.

Who. Wood Dust, IARC Monographs Evaluation of Carcinogenic Risks to Humans. vol. 62. 423 pages. 1995.

Youlden et al. "International comparisons of the incidence and mortality of sinonasal cancer." Cancer epidemiology. 37:770-779. 2013.

Zuskin et al. "Respiratory symptoms and lung function in hemp workers." British journal of industrial medicine. 47:627-632. 1990.

(56) References Cited

OTHER PUBLICATIONS

Zuskin et al. "Respiratory symptoms and ventilatory capacity in workers in a vegetable pickling and mustard production facility." International archives of occupational and environmental health. 64:457-461. 1993.

Zuskin et al. Respiratory findings in spice factory workers. Archives of Environmental Health: An International Journal. 43:335-339. 1988a.

Lin et al. "Dry Deposition Velocities as a Function of Particle Size in the Ambient Atmosphere". Aerosol Science and Technology. 20:239-252. 1994.

Yu et al. "Neural model of disinhibitory interactions in the modified Poggendorff illusion." Biol Cybern. 98:75-85. 2008.

Yu et al. "Angular Disinhibition Effect in a Modified Poggendorff Illusion". In Proceedings of the 26th annual conference of the Cognitive Science Society. pp. 1500-1505. Aug. 5, 2004.

\* cited by examiner

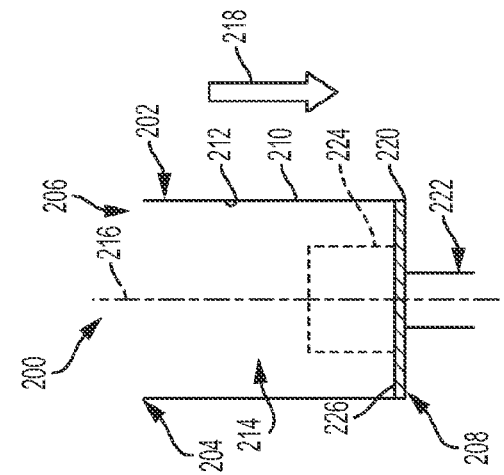
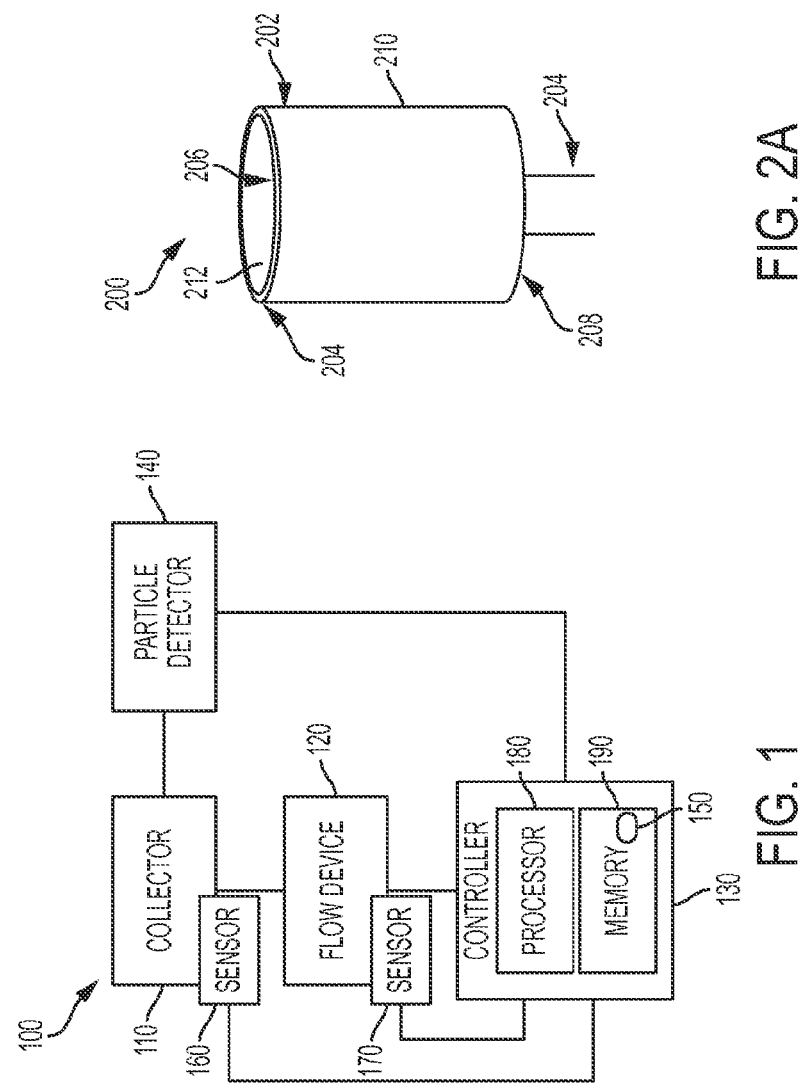
FIG. 1
FIG. 2A
FIG. 2B

PORTABLE PARTICLE SPECTROMETER

CROSS-REFERENCE TO RELATED APPLICATIONS

This application claims the benefit under 35 U.S.C. §119 to U.S. Provisional Application Ser. No. 62/066,644, filed Oct. 21, 2014, which is hereby incorporated by reference herein in its entirety for all purposes.

STATEMENT REGARDING FEDERALLY SPONSORED RESEARCH OR DEVELOPMENT

This invention was made with government support under Grant No. R21 OH010117 awarded by the Centers for Disease Control. The government has certain rights in the invention.

TECHNICAL FIELD

The present disclosure generally relates to particle sampling systems and methods. More specifically, the present disclosure relates to systems and methods for detecting and characterizing particles in an aerosol.

BACKGROUND

Large, inhalable particles are present in the workplace, yet few instruments exist to count and size such particles in situ. Inhalable aerosol exposure can be evaluated using mass-based samplers such as the IOM or Button sampler, but these devices do not provide information on particle size distributions. Size-resolved samplers such as cascade impactors or the Aerodynamic Particle Sizer are limited to particle sizes<20 micrometers (μm) due to difficulties with particle aspiration and transmission losses.

Inhalable particles are defined as those that penetrate into the head airway region and beyond. Ogden and Birkett (Ogden and Birkett 1975) were the first to present the idea of the human head as a blunt aerosol sampler and to demonstrate that the head does not effectively inhale particles of all sizes. The inhalable particulate mass (IPM) criterion was subsequently developed to describe the fractional sampling efficiency of the human head (the inhaled fraction, or IF) as a function of particle aerodynamic diameter:

$$IF = 0.5 * (1 + \exp(-0.06 * d_{ae})) \quad (1)$$

for wind speeds<4 m s$^{-1}$ and particles<100 μm (Soderholm 1989).

Exposure to inhalable aerosols is traditionally assessed using time-integrated personal samplers with gravimetric analyses to determine dust concentration (Eller and Cassinelli 1994). The 37-mm cassette is the most commonly used personal sampler in the US for industrial hygiene sampling. However, the 37-mm cassette under-samples large particles (>20 μm), relative to the human head (Kenny et al. 1999; Kenny et al. 1997). Compared with the 37-mm cassette, the IOM and Button samplers have sampling efficiencies that better match the IPM criterion (Grinshpun et al. 1995; Kalatoor et al. 1995; Mark and Vincent 1986). All of these size-selective samplers are limited; they do not report size distributions, only mass concentrations. Instruments capable of reporting the size distribution of aerosols exist, such as the Aerodynamic Particle Sizer (APS), Scanning Mobility Particle Sizer (SMPS) and various cascade impactors; however, these instruments are limited to particle sizes less than about 20 μm in aerodynamic diameter.

The aerodynamic particle sizer (APS) reports concentration and size distribution for airborne particles from 0.5 to 20 μm and has been extensively used in laboratory and field studies (Armendariz and Leith 2002; Baron 1986; Chen et al. 1985; Görner et al. 2010; Marshall et al. 1991; Peters et al. 2006). Although extremely useful, the APS provides size distribution information for only a fraction of the inhalable range. At approximately 10 μm, the APS begins to experience issues with particle transmission efficiency into the detector (Volckens and Peters 2005).

Gibson, Vincent and Mark (Gibson et al. 1987) developed the personal inhalable dust spectrometer (PIDS), an eight-stage, cascade impactor with an entry designed to match the IPM criterion. The PIDS has been used to characterize the size distribution of aerosol particles in coal mines, bakeries, and primary lead smelters, where most of the mass is coarse. Mass median diameters of 41.6, 60.7, 67.3 and 71.4 μm were found in ore storage and milling, sinter pants, blast furnace, and drossing areas, respectively (Spear et al. 1998). Bimodal distributions were found in an automated bakery, egg powdery, cement factory, steel mill, spice factory, and in furniture carpentry, with large mass median diameters for the coarser mode ranging from 14-59 μm (Lidén et al. 2000). These studies demonstrate the presence of coarse dust in workplaces, with mass median diameters often above 40 μm.

Although the measurement of inhalable particles is difficult, accurate knowledge of their concentration and size is necessary to assess exposure and dose. Substantial differences exist in deposition to the oral, nasal, pharyngeal and laryngeal regions for particles between 10 and 50 μm (Cheng et al. 1999); thus, the health effects of these particles can be substantially different. Particle deposition in the tracheobronchial region could potentially cause health effects such as asthma and bronchogenic cancer. Particles depositing in the oronasal cavities could result in health effects centered primarily in the upper respiratory region.

A high prevalence of occupational illnesses is related to inhalable-particle exposures. For example, occupational rhinitis occurs three times more frequently in occupational settings than occupational asthma (Bush et al. 1998). Exposure to animal dander (Kup 1985; Slovak and Hill 1981), flours (Moscato et al. 2008), wood dust (Kanerva and Vaheri 1993; Moscato et al. 2008), textile dust (Slavin 2003), food, spices, organic dusts, latex and chemicals have all been associated with occupational rhinitis, as has exposure to pesticides (Slager et al. 2009). Furriers, spice workers, vegetable pickers, hemp workers, and grain handlers all have increased prevalence rates for self-reported sinusitis (El Karim et al. 1986; Zuskin et al. 1990; Zuskin et al. 1993; Zuskin et al. 1988a; b).

Sinonasal tumors are rare, but of all cancers have the second highest fraction attributable to occupational exposures (Rushton et al. 2012; Youlden et al. 2013). Exposure to wood dust (Andersen et al. 1977; Kleinsasser and Schroeder 1988; Pesch et al. 2008; WHO 1995), leather dust (Bonneterre et al. 2007), nickel compounds, radium-226, radium-228 and their decay products, and acids used in isopropyl alcohol production are all known risk factors for sinonasal cancer (Baan et al. 2009; El Ghissassi et al. 2009; Straif et al. 2009). Textile dust (Luce et al. 1997) and hexavalent chromium are possible risk factors for sinonasal tumors as well, but evidence is limited.

Retrospective epidemiological studies, exposure assessments, and the design of industrial hygiene controls are all hindered by this inability to monitor inhalable particles accurately. The objective of this study, therefore, was to develop a particle separator capable of characterizing concentrations and size distributions of inhalable aerosol particles from 30 to 100 μm in aerodynamic diameter. The designs described here focus on sampling in calm air environments, as mean indoor wind speeds are generally less than 0.3 m s-1 in most workplaces (Baldwin and Maynard 1998).

SUMMARY

Embodiments of the disclosed subject matter include a system for characterizing particles in an aerosol. Embodiments of the system may be capable of measuring the concentration and size distribution of particles in an aerosol having an aerodynamic diameter of at least about 10 μm (e.g., particles from about 10 to about 100 μm in aerodynamic diameter). In embodiments, the system may include a collection container configured to collect settling particles based on the principles of an upflow elutriator; and, in embodiments, a housing may be used to reduce the potentially adverse effects of an upward-facing jet to separate particles from a quiescent airstream.

In an Example 1, a system for characterizing particles in an aerosol, the system comprising: a collection container comprising: a first end having an opening; a second end, wherein the collection container is configured to be oriented such that an axis of symmetry extending from the first end to the second end is oriented substantially in a direction of gravitational settling of the particles; and a collection container wall extending between the first end and the second end, the collection container wall having an inner surface defining a collection chamber; a first flow device coupled to the second end and configured to provide a first fluid flow from the second end toward the first end, wherein the first fluid flow is configured such that particles having a first aerodynamic diameter settle into a measurement region of the collection tube; and a particle detector operatively coupled to the collection container, wherein the particle detector is configured to detect at least one particle within the measurement region of the collection chamber.

In an Example 2, the system of Example 1, wherein the particle detector includes a collection surface disposed at or near the second end of the collection container.

In an Example 3, the system of Example 2, wherein the collection surface comprises a surface of a filter.

In an Example 4, the system of Example 1, wherein the particle detector comprises a laser induced breakdown spectroscopy (LIBS) system, the LIBS system comprising: a LIBS laser generator operatively coupled to the collection container and configured to provide a LIBS laser beam that produces a plasma within the collection chamber such that the produced plasma causes an optical emission when the at least one particle passes through the plasma; and a LIBS spectrometer operatively coupled to the collection container and configured to receive the optical emission and determine, based on the optical emission, a composition of the at least one particle.

In an Example 5, the system of Example 4, the particle detector further comprising a trigger laser system, the trigger laser system comprising a trigger laser generator operatively coupled to the collection container and configured to provide a trigger laser beam within the collection chamber.

In an Example 6, the system of Example 5, the trigger laser system further comprising a trigger photodetector operatively coupled to the collection container and configured to detect at least one of an interruption of the trigger laser beam by the at least one particle and Mie-scattered light produced when the at least one particle passes through the trigger laser beam.

In an Example 7, the system of any of Examples 5 and 6, the trigger laser system further configured to initiate, in response to detecting the at least one particle, detection by the LIBS laser generator and the LIBS spectrometer.

In an Example 8, the system of any of Examples 1-7, the particle detector further comprising a Mie scattering particle counting system, the Mie scattering particle counting system comprising: a Mie scattering laser generator operatively coupled to the collection container and configured to provide a Mie scattering laser sheet in the collection chamber; and a Mie scattering photodetector operatively coupled to the collection container and configured to (1) produce a signal in response to detecting light scattered off of the at least one particle when the at least one particle intersects the Mie scattering laser sheet, (2) determine whether the signal exceeds a threshold, and (3) register a count if the signal exceeds the threshold.

In an Example 9, the system of any of Examples 1-8, further comprising: a housing, wherein at least a portion of the collection container is disposed within the housing, the housing comprising: a first housing end having a cap disposed above, and spaced apart from, the first end of the collection container, the cap having an inlet aperture defined therein; a second housing end; and a housing wall extending downward from the first housing end such that at least a portion of the housing wall is positioned external to, and spaced apart from, the collection container wall, thereby forming a gap between an outside surface of the collection container wall and an inside surface of the housing wall; and a second flow device operatively coupled to the housing and configured to provide a second fluid flow, within the gap, away from the first housing end, thereby creating a fluid stagnation region above the first end of the collection container.

In an Example 10, the system of Example 9, further comprising a controller configured to control the first and second flow devices to create the fluid stagnation region.

In an Example 11, the system of Example 10, wherein the controller is configured to: receive a first user input specifying the first aerodynamic diameter; adjust, in response to receiving the first user input, at least one of the first and second flow devices to configure the system to collect particles having the first aerodynamic diameter; receive a second user input specifying a second aerodynamic diameter; and adjust, in response to receiving the second user input, at least one of the first and second flow devices to configure the system to collect particles having the second aerodynamic diameter.

In an Example 12, the system of any of Examples 1-11, wherein the first aerodynamic diameter is at least ten microns.

In an Example 13, the system of Example 12, wherein the first aerodynamic diameter is no less than ten microns and no greater than one hundred microns.

In an Example 14, a system for characterizing particles in an aerosol, the system comprising: a collection container comprising: a first end having an opening; a second end, wherein the collection container is configured to be oriented such that an axis of symmetry extending from the first end to the second end is oriented substantially in a direction of gravitational settling of the particles; and a collection container wall extending between the first end and the second end, the collection container wall having an inner surface defining a collection chamber; a first flow device coupled to the second end and configured to provide a first fluid flow from the second end toward the first end, wherein the first fluid flow is configured such that particles having a first aerodynamic diameter settle into a measurement region of the collection tube; a particle detector operatively coupled to the collection container, wherein the particle detector is configured to detect at least one particle within the measurement region of the collection chamber; a housing, wherein at least a portion of the collection container is disposed within the housing, the housing comprising: a first housing end having a cap disposed above, and spaced apart from, the first end of the collection container, the cap having an inlet aperture defined therein; a second housing end; and a housing wall extending downward from the first housing end such that at least a portion of the housing wall is positioned external to, and spaced apart from, the collection container wall, thereby forming a gap between an outside surface of the collection container wall and an inside surface of the housing wall; and a second flow device operatively coupled to the housing and configured to provide a second fluid flow, within the gap, away from the first housing end, thereby creating a fluid stagnation region above the first end of the collection container.

In an Example 15, the system of Example 14, further comprising a controller configured to control the first and second flow devices to create the fluid stagnation region.

In an Example 16, a system for characterizing particles in an aerosol, the system comprising: a collection container comprising: a first end having an opening; a second end, wherein the collection container is configured to be oriented such that an axis of symmetry extending from the first end to the second end is oriented substantially in a direction of gravitational settling of the particles; and a collection container wall extending between the first end and the second end, the collection container wall having an inner surface defining a collection chamber; a first flow device coupled to the second end and configured to provide a first fluid flow from the second end toward the first end, wherein the first fluid flow is configured such that particles having a first aerodynamic diameter settle into a measurement region of the collection tube; and a particle detector operatively coupled to the collection container, wherein the particle detector is configured to detect at least one particle within the measurement region of the collection chamber.

In an Example 17, the system of Example 16, wherein the particle detector includes a collection surface disposed at or near the second end of the collection container.

In an Example 18, the system of Example 17, wherein the collection surface comprises a surface of a filter.

In an Example 19, the system of Example 16, wherein the particle detector comprises a laser induced breakdown spectroscopy (LIBS) system, the LIBS system comprising: a LIBS laser generator operatively coupled to the collection container and configured to provide a LIBS laser beam that produces a plasma within the collection chamber such that the produced plasma causes an optical emission when the at least one particle passes through the plasma; and a LIBS spectrometer operatively coupled to the collection container and configured to receive the optical emission and determine, based on the optical emission, a composition of the at least one particle.

In an Example 20, the system of Example 19, the particle detector further comprising a trigger laser system, the trigger laser system comprising a trigger laser generator operatively coupled to the collection container and configured to provide a trigger laser beam within the collection chamber.

In an Example 21, the system of Example 20, the trigger laser system further comprising a trigger photodetector operatively coupled to the collection container and configured to detect at least one of an interruption of the trigger laser beam by the at least one particle and Mie-scattered light produced when the at least one particle passes through the trigger laser beam.

In an Example 22, the system of Example 21, the trigger laser system further configured to initiate, in response to detecting the at least one particle, detection by the LIBS laser generator and the LIBS spectrometer.

In an Example 23, the system of Example 16, the particle detector further comprising a Mie scattering particle counting system, the Mie scattering particle counting assembly comprising: a Mie scattering laser generator operatively coupled to the collection container and configured to provide a Mie scattering laser sheet in the collection chamber; and a Mie scattering photodetector operatively coupled to the collection container and configured to (1) produce a signal in response to detecting light scattered off of the at least one particle when the at least one particle intersects the Mie scattering laser sheet, (2) determine whether the signal exceeds a threshold, and (3) register a count if the signal exceeds the threshold.

In an Example 24, the system of Example 16, further comprising: a housing, wherein at least a portion of the collection container is disposed within the housing, the housing comprising: a first housing end having a cap disposed above, and spaced apart from, the first end of the collection container, the cap having an inlet aperture defined therein; a second housing end; and a housing wall extending downward from the first housing end such that at least a portion of the housing wall is positioned external to, and spaced apart from, the collection container wall, thereby forming a gap between an outside surface of the collection container wall and an inside surface of the housing wall; and a second flow device operatively coupled to the housing and configured to provide a second fluid flow, within the gap, away from the first housing end, thereby creating a fluid stagnation region above the first end of the collection container.

In an Example 25, the system of Example 24, further comprising a controller configured to control the first and second flow devices to create the fluid stagnation region.

In an Example 26, the system of Example 24, wherein the controller is configured to: receive a first user input specifying the first aerodynamic diameter; adjust, in response to receiving the first user input, at least one of the first and second flow devices to configure the system to collect particles having the first aerodynamic diameter; receive a second user input specifying a second aerodynamic diameter; and adjust, in response to receiving the second user input, at least one of the first and second flow devices to configure the system to collect particles having the second aerodynamic diameter.

In an Example 27, the system of Example 16, wherein the first aerodynamic diameter is at least ten microns.

In an Example 28, the system of Example 16, wherein the first aerodynamic diameter is no less than ten microns and no greater than one hundred microns.

In an Example 29, a system for characterizing particles in an aerosol, the system comprising: a collection container comprising: a first end having an opening; a second end, wherein the collection container is configured to be oriented such that an axis of symmetry extending from the first end to the second end is oriented substantially in a direction of gravitational settling of the particles; and a collection container wall extending between the first end and the second end, the collection container wall having an inner surface defining a collection chamber; a first flow device coupled to the second end and configured to provide a first fluid flow from the second end toward the first end, wherein the first fluid flow is configured such that particles having a first aerodynamic diameter settle into a measurement region of the collection tube; a particle detector operatively coupled to the collection container, wherein the particle detector is configured to detect at least one particle within the measurement region of the collection chamber; a housing, wherein at least a portion of the collection container is disposed within the housing, the housing comprising: a first housing end having a cap disposed above, and spaced apart from, the first end of the collection container, the cap having an inlet aperture defined therein; a second housing end; and a housing wall extending downward from the first housing end such that at least a portion of the housing wall is positioned external to, and spaced apart from, the collection container wall, thereby forming a gap between an outside surface of the collection container wall and an inside surface of the housing wall; and a second flow device operatively coupled to the housing and configured to provide a second fluid flow, within the gap, away from the first housing end, thereby creating a fluid stagnation region above the first end of the collection container.

In an Example 30, the system of Example 29, further comprising a controller configured to control the first and second flow devices to create the fluid stagnation region.

In an Example 31, a method for characterizing particles in an aerosol, the method comprising: providing a first fluid flow in a collection chamber defined within a collection container, the collection container comprising a first end having an opening, a second end, and a collection container wall extending between the first end and the second end, wherein the first fluid flow is provided in a direction from the second end toward the first end; and detecting at least one particle within a measurement region of the collection chamber.

In an Example 32, the method of Example 31, further comprising providing a second fluid flow within a housing, wherein at least a portion of the collection container is disposed within the housing, the housing comprising: a first housing end having a cap disposed above, and spaced apart from, the first end of the collection container, the cap having an inlet aperture defined therein; a second housing end; and a housing wall extending downward from the first housing end such that at least a portion of the housing wall is positioned external to, and spaced apart from, the collection container wall, thereby forming a gap between an outside surface of the collection container wall and an inside surface of the housing wall; wherein the second fluid flow is provided in a direction away from the first housing end, thereby creating a fluid stagnation region above the first end of the collection container.

In an Example 33, the method of Example 31, wherein detecting the at least one particle within the measurement region of the collection chamber comprises: providing a laser induced breakdown spectroscopy (LIBS) laser beam within the collection chamber, wherein the LIBS laser beam produces a plasma within the collection chamber such that the produced plasma causes an optical emission when the at least one particle passes through the plasma; receiving the optical emission; and determining, based on the optical emission, a composition of the at least one particle.

In an Example 34, the method of Example 31, wherein detecting the at least one particle within the measurement region of the collection chamber comprises: providing at least one of a trigger laser beam and a Mie scattering laser sheet within the collection chamber; detecting Mie-scattered light; and detecting, based on the Mie-scattered light, the at least one particle.

In an Example 35, the method of Example 31, wherein the at least one particle has an aerodynamic diameter of at least ten microns.

BRIEF DESCRIPTION OF THE DRAWINGS

FIG. 1 is a block diagram of a system for characterizing particles in an aerosol, in accordance with embodiments of the present disclosure.

FIG. 2A is a perspective side view of a collector, in accordance with embodiments of the present disclosure.

FIG. 2B is a cross-sectional side view of the collector of FIG. 2A, in accordance with embodiments of the present disclosure.

Figure 3:
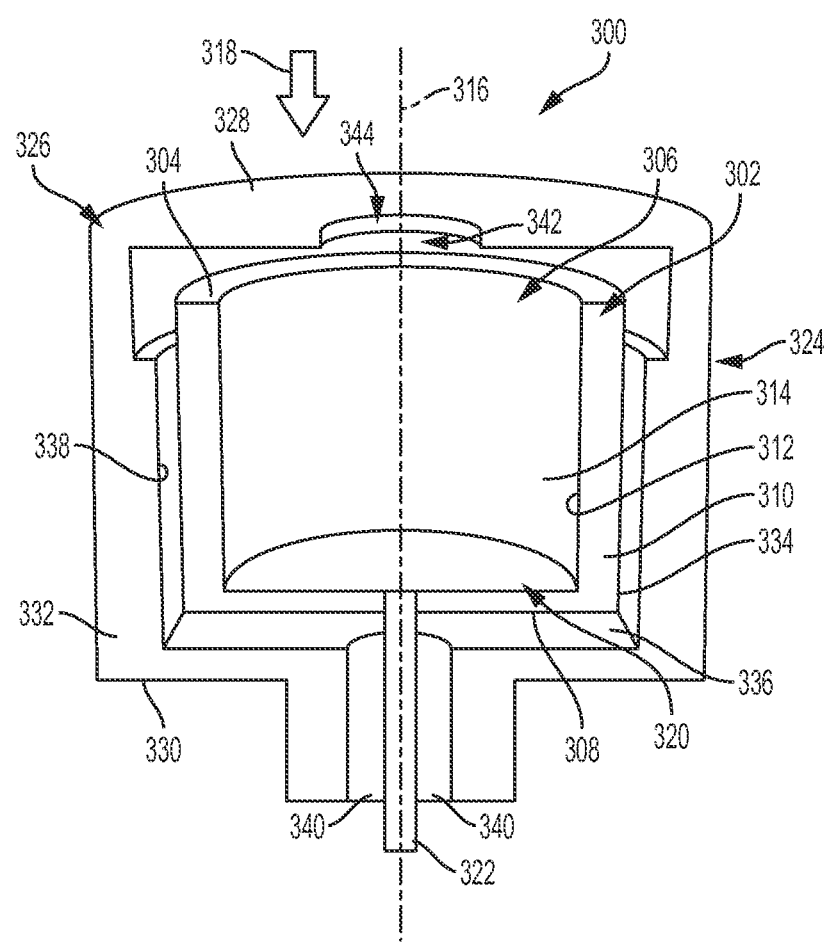
FIG. 3 is a cross-sectional perspective view of another collector, in accordance with embodiments of the present disclosure.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Although the term "block" may be used herein to connote different elements illustratively employed, the term should not be interpreted as implying any requirement of, or particular order among or between, various steps disclosed herein unless and except when explicitly referring to the order of individual steps.

DETAILED DESCRIPTION

FIG. 1 is a block diagram of a system 100 for characterizing particles in an aerosol, in accordance with embodiments of the disclosure. As shown, the system includes a collector 110, a flow device 120 configured to provide a fluid flow to the collector 110, a controller 130 configured to control the flow device 120, and a particle detector 140 configured to detect particles and/or determine characteristics of particles collected using the collector 110. According to embodiments, the system 100 may be configured to detect particles in an aerosol settling under the force of gravity. Throughout this disclosure, the term "aerosol" can mean any combination of particles of any size and gas of any type such as, for example, a colloid, a suspension, and/or the like. While this disclosure discusses using the system 100 to characterize particles in an aerosol, embodiments of the system 100 may also, or alternatively, be used to characterize particles in other fluid media including, but not limited to, a liquid, a plasma, and/or the like. Further, the system 100 may characterize particles by detecting the particles, counting the particles, determining sizes (e.g., aerodynamic diameters) of particles, measuring a size distribution of particles, determining a composition of particles, determining a particle type distribution, and/or the like.

According to embodiments, and as is further described below, the collector 110 may include a collection container that is based on the principles of a vertical elutriator. That is, for example, the collector 110 may operate by directing a clean fluid flow (e.g., a first fluid flow) upward through a vertically-oriented collection container. According to embodiments, the collector 110 may incorporate an additional fluid flow (e.g., a second fluid flow) drawn laterally outward along the sides of the collection container. In embodiments, for example, the collector 110 may include a housing disposed over at least a portion of the outside of the collection container such that a gap is formed between the inside of the housing and the outside of the collection container. By drawing an approximately equal flow of fluid laterally out and down around the collection container in the gap, the fluid jet formed at the top of the collection container is pulled radially outward, creating a stagnation point above the collection container. In this manner, smaller particles generally are transferred radially outward and away from the top of the collection container, whereas larger particles generally enter the collection container and settle into the measurement region.

The terms "up," and "upward," and variations thereof, are used throughout this disclosure to refer, at least approximately, to a direction opposite a direction of gravitational settling of particles in the context of the environment to which the term refers. Similarly, the terms "down," and "downward," and variations thereof, are used throughout this disclosure to refer, at least approximately, to a direction of gravitational settling of particles in the context of the environment to which the term refers; and the term "vertical," and variations thereof, is used to refer to an orientation corresponding to the direction of gravitational settling of particles in the context of the environment to which the term refers.

The flow device 120 may be configured to provide the fluid flow within the collection container, and may include any type of fan, blower, pump, and/or the like. In embodiments, the system 100 may include more than one flow device 120. For example, the system may include a flow device 120 for providing a first fluid flow, and a second flow device 120 for providing a second fluid flow. In general, if a particle's terminal settling velocity is greater than the upward fluid flow velocity in the collection container, the particle will settle into a measurement region of the collection container, which may include, for example, a filter at the base of the collection container. In general, if the particle's terminal settling velocity is less than the fluid flow velocity in the collection container, the particle will be blown upward and out of the collection container.

It should be understood that, while the fluid flow velocity within the collection container may be approximately uniform, it may not be perfectly uniform and may vary depending on the location in the container. Thus, the collection container may be configured to have a measurement region into which particles having an aerodynamic diameter that satisfies a condition are likely to settle. The measurement region may include a surface (e.g., on a filter), a volume, and/or the like. In this manner, the fluid flow velocity in the collection container may be varied to select a minimum particle size capable of reaching the measurement region. For example, fluid flow velocities may be selected to be approximately equal to the terminal settling velocity of particles having aerodynamic diameters greater than 10 μm (e.g., 30 μm, 40 μm, 50 μm, 60 μm, 70 μm, 80 μm, and/or the like), between 10 μm and 100 μm, and/or the like. That is, for example, the condition may refer to a particular upper threshold, lower threshold, and/or range.

In embodiments, the controller 130 may be configured to control the flow device 120 to vary the fluid flow velocity. In embodiments, the controller 130 may include a control module 150 configured to vary the fluid flow velocity in response to user input, computer-readable instructions, an output of a feedback control loop, and/or the like. As such, the system 100 may also include sensors 160 and 170, operatively coupled to the collector 110 and the flow device 120, respectively. The sensors may be configured to directly or indirectly measure fluid flow velocity, and may include any number of different types of sensors capable of facilitating that measurement. In embodiments, the controller 130 may be configured to determine a composition of the fluid, a temperature of the fluid, force of gravity, wind speed, density, pressure, and/or any number of other characteristics of the fluid, ambient environment, and/or the like. These characteristics may be used by the controller to determine the appropriate fluid flow velocity to direct the flow device 120 to provide a certain fluid flow velocity, and may be determined based on user input, input from the sensors 160 and 170, input from additional sensors (not shown), and/or the like.

The controller 130 may also be operatively coupled to the particle detector 140. In embodiments, for example, the controller 130 may communicate with the particle detector 140 to coordinate measurements, control the particle detector 140, and/or the like. For example, the controller 130 may facilitate altering one or more operational parameters of the particle detector 140 based on fluid flow velocity, and/or any other information. As described more fully below, with reference to FIG. 5, the particle detector 140 may include a filter and/or any number of different types of spectroscopy systems such as, for example, laser systems. In embodiments, the particle detector 140 may include a microscope, camera, and/or other viewing/imaging devices.

As shown in FIG. 1, the controller 130 may be implemented on a computing device that includes a processor 180 and a memory 190. In embodiments, the controller 130 may be integrated with the collector 110, the flow device 120, and/or the particle detector 140 and may include one or more Field Programmable Gate Arrays (FPGAs), one or more Programmable Logic Devices (PLDs), one or more Complex PLDs (CPLDs), one or more custom Application Specific Integrated Circuits (ASICs), one or more dedicated processors (e.g., microprocessors) and/or the like. Although the controller 130 is referred to herein in the singular, the controller 130 may be implemented in multiple server instances (e.g., as a server cluster), distributed across multiple computing devices, instantiated within multiple virtual machines, and/or the like. The control module 150 may be stored in the memory 190. In embodiments, the processor 180 executes the control module 150, which may facilitate control of the flow device 120 and/or the particle detector 140.

According to embodiments, various components of the system 100, illustrated in FIG. 1, may be implemented on one or more computing devices. For example, in embodiments, the flow device 120, the controller 130, and/or particle detector 140 may include, be included within, and/or be operatively coupled to a computing device such as the computing device described herein with respect to the controller 130. A computing device may include any type of computing device suitable for implementing embodiments of the invention. Examples of computing devices include specialized computing devices or general-purpose computing devices such "workstations," "servers," "laptops," "desktops," "tablet computers," "hand-held devices," and the like, all of which are contemplated within the scope of FIG. 1 with reference to various components of the system 100.

In embodiments, a computing device includes a bus that, directly and/or indirectly, couples the following devices: a processor, a memory, an input/output (I/O) port, an I/O component, and a power supply. Any number of additional components, different components, and/or combinations of components may also be included in the computing device. The bus represents what may be one or more busses (such as, for example, an address bus, data bus, or combination thereof). Similarly, in embodiments, the computing device may include a number of processors, a number of memory components, a number of I/O ports, a number of I/O components, and/or a number of power supplies. Additionally any number of these components, or combinations thereof, may be distributed and/or duplicated across a number of computing devices.

In embodiments, the memory 190 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; or any other medium that can be used to store information and can be accessed by a computing device such as, for example, quantum state memory, and the like. In embodiments, the memory 190 stores computer-executable instructions for causing the processor 180 to implement aspects of embodiments of system components discussed herein and/or to perform aspects of embodiments of methods and procedures discussed herein. Computer-executable instructions may include, for example, computer code, machine-useable instructions, and the like such as, for example, program components (e.g., the control module 150) capable of being executed by one or more processors associated with a computing device. Program components may be programmed using any number of different programming environments, including various languages, development kits, frameworks, and/or the like. Some or all of the functionality contemplated herein may also be implemented in hardware and/or firmware.

The illustrative system 100 shown in FIG. 1 is not intended to suggest any limitation as to the scope of use or functionality of embodiments of the present disclosure. Neither should the illustrative system 100 be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the present disclosure.

FIG. 2A is a perspective side view of a collector 200, in accordance with embodiments of the disclosure; and FIG. 2B is a cross-sectional side view of the collector 200, in accordance with embodiments of the disclosure. The collector 200 may be, for example, identical to, or similar to, the collector 110 described above and depicted in FIG. 1. As shown in FIGS. 2A and 2B, the collector 200 comprises a collection container 202 including a first end 204 having an opening 206; a second end 208; and a collection container wall 210 extending between the first end 204 and the second end 208. The collection container wall 210 includes an inner surface 212 defining a collection chamber 214. According to embodiments, the collection container 202 may be configured to be oriented such that an axis of symmetry 216 extending from the first end 204 to the second end 208 is oriented at least approximately in a direction 218 of gravitational settling of particles to be measured.

As shown in FIG. 2B, a filter 220 may be disposed at or near the second end 208 of the collection container 210, within the collection chamber 214. In embodiments, the filter 220 may be configured to filter fluid provided, via a fluid flow conduit 222, by a flow device (e.g., the flow device 120 depicted in FIG. 1). Additionally, the filter 220 may be configured to cause a distribution of the fluid flow entering the collection container 202 from the fluid flow conduit 222, thereby providing an at least approximately uniform fluid flow upward through the filter 220. Thus, for example, as illustrated, the fluid flow conduit 222 may be narrower than the collection container 202, while being configured to provide an at least approximately uniform fluid flow from the second end 208 of the collection container 202. In embodiments, any other structure (e.g., a mesh, a screen, and/or the like) may be used in lieu of, or in addition to, the filter 220 for fluid cleaning and flow distribution. Additionally, as explained above, with reference to FIG. 1, the collection container 202 may include a measurement region 224. As shown, the measurement region 224 may include a volumetric region within the collection container 202. In embodiments, the measurement region 224 may include a region of a surface such as, for example, a region on an upper surface 226 of the filter 220 that operates as a collection surface.

In embodiments, the collection container wall 210 may be configured according to any number of different shapes. For example, the collection container wall 210 may be configured in the shape of a cylinder. That is, in embodiments, a cross section of the collection container wall 210 taken perpendicular to the axis 216 may be at least approximately circular. In embodiments, a cross section taken perpendicular to the axis 216 may be at least approximately square, rectangular, elliptical, and/or the like. Additionally, according to embodiments, the collection container 202 may be constructed using any number of different materials.

The illustrative collector 200 shown in FIGS. 2A and 2B is not intended to suggest any limitation as to the scope of use or functionality of embodiments of the present disclosure. Neither should the illustrative collector 200 be interpreted as having any dependency or requirement related to any single component or combination of components illustrated therein. Additionally, various components depicted in FIGS. 2A and 2B may be, in embodiments, integrated with various ones of the other components depicted therein (and/or components not illustrated), all of which are considered to be within the ambit of the present disclosure.

FIG. 3 is a cross-sectional side perspective view of a collector 300, in accordance with embodiments of the disclosure. The collector 300 may be, for example, identical to, or similar to, the collector 110 described above and depicted in FIG. 1. As shown in FIG. 3, the collector 300 comprises a collection container 302 including a first end 304 having an opening 306; a second end 308; and a collection container wall 310 extending between the first end 304 and the second end 308. The collection container wall 310 includes an inner surface 312 defining a collection chamber 314. According to embodiments, the collection container 302 may be configured to be oriented such that an axis of symmetry 316 extending from the first end 304 to the second end 308 is oriented at least approximately in a direction 318 of gravitational settling of particles to be measured.

As shown in FIG. 3, a filter 320 may be disposed at or near the second end 308 of the collection container 302, within the collection chamber 314. In embodiments, the filter 320 may be configured to filter fluid provided, via a fluid flow conduit 322, by a flow device (e.g., the flow device 120 depicted in FIG. 1). Additionally, the filter 320 may be configured to cause a distribution of the fluid flow entering the collection chamber 314 from the fluid flow conduit 322, thereby providing an at least approximately uniform fluid flow upward through the filter 320. In embodiments, any other structure (e.g., a mesh, a screen, and/or the like) may be used in lieu of, or in addition to, the filter 320 for fluid cleaning and flow distribution. Additionally, as explained above, with reference to FIG. 1, the collection container 302 may include a measurement region (not shown in FIG. 3).

Additionally, in embodiments, the collection container wall 310 may be configured according to any number of different shapes. For example, in embodiments, a cross section taken perpendicular to the axis 316 may be at least approximately circular, square, rectangular, and/or the like. As shown, the collector 300 also includes a housing 324. As shown, in embodiments, at least a portion of the collection container 302 is disposed within the housing 324. The housing 324 includes a first housing end 326 having a cap 328 disposed above, and spaced apart from, the first end 304 of the collection container 302. The housing 324 also includes a second housing end 330, and a housing wall 332 extending downward from the first housing end 326 such that at least a portion of the housing wall 332 is positioned external to, and spaced apart from, an outside surface 334 of the collection container wall 310, thereby forming a gap 336 between the outside surface 334 of the collection container wall 310 and an inside surface 338 of the housing wall 332.

One or more additional flow devices (not shown) may be operably coupled to the second housing via one or more additional fluid flow conduits 340 to provide a fluid flow away from the first housing end 326, downward in the gap 336, thereby creating a fluid stagnation region 342 above the first end 304 of the collection container 302. As illustrated in FIG. 3, the fluid stagnation region 342 may correspond to an inlet aperture 344 defined in the cap 328 of the first housing end 326. In embodiments, the inlet aperture 344 may be centered about the axis 316 such that particles settling through the inlet aperture 344 may have a tendency to settle in a more central portion of the collection container 302. In embodiments, the fluid stagnation region 342 may be at least partially disposed within the inlet aperture 344, below the inlet aperture 344, and/or above the inlet aperture. The size and shape of the inlet aperture 344 may be configured to produce a desired result based, for example, on the size and/or shape of the collection container 302, the housing 324, and/or the like. A controller (e.g., the controller 130 depicted in FIG. 1) may be configured to control the first and second flow devices to create the fluid stagnation region.

As with the collection container 302, embodiments of the housing wall 332 may be configured according to any number of different shapes. For example, the housing wall 332 may be configured in the shape of a cylinder. That is, in embodiments, a cross section of the housing wall 332 taken perpendicular to the axis 316 may be at least approximately circular. In embodiments, a cross section taken perpendicular to the axis 316 may be at least approximately square, rectangular, elliptical, and/or the like. For example, the housing wall 332 may be configured according to the same shape as that of the collection container wall 310. The gap 336 may be disposed between at least a portion of the outside surface 334 of the collection container wall 310 and the inside surface 338 of the housing wall 332. In embodiments, the gap 336 may refer to one or more channels disposed in the housing wall 332. Additionally, according to embodiments, the housing wall 332 may be constructed using any number of different materials.

The illustrative collector 300 shown in FIG. 3 is not intended to suggest any limitation as to the scope of use or functionality of embodiments of the present disclosure. Neither should the illustrative collector 300 be interpreted as having any dependency or requirement related to any single component or combination of components illustrated therein. Additionally, various components depicted in FIG. 3 may be, in embodiments, integrated with various ones of the other components depicted therein (and/or components not illustrated), all of which are considered to be within the ambit of the present disclosure.

Figure 4:
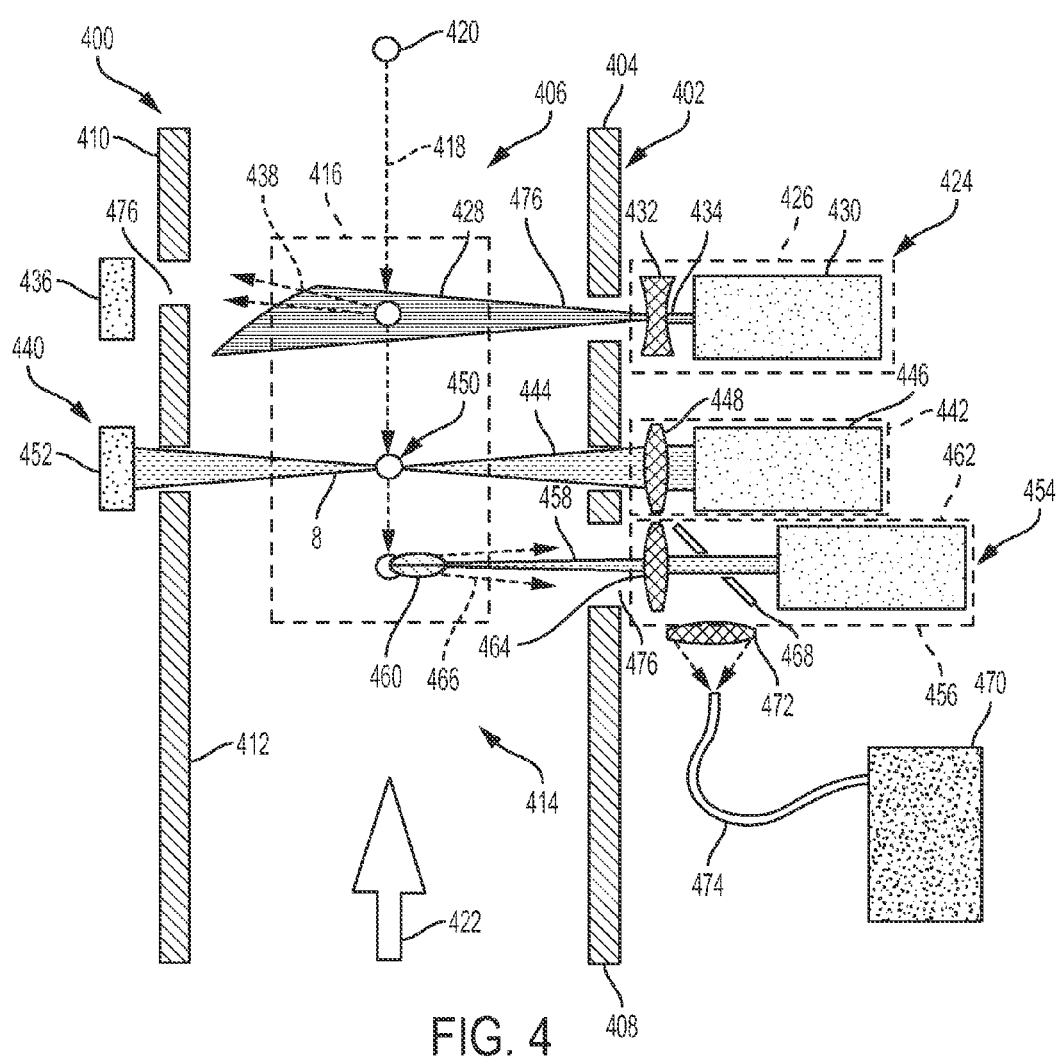
FIG. 4 is a schematic diagram of a system for characterizing particles in an aerosol, in accordance with embodiments of the present disclosure.

FIG. 4 is a schematic illustration of a system 400 for characterizing particles in an aerosol, in accordance with embodiments of the disclosure. According to embodiments, the system may be, be similar to, include, or be included in, the system 100 depicted in FIG. 1. The system 400 includes a collection container 402 that includes a first end 404 having an opening 406; a second end 408; and a collection container wall 410 extending between the first end 404 and the second end 408. The collection container wall 410 includes an inner surface 412 defining a collection chamber 414. The collection chamber 414 includes a measurement region 416, which is depicted as a volumetric region 416. According to embodiments, the collection container 402 may be, be similar to, include, or be included in, the collector 110 depicted in FIG. 1, the collector 200 depicted in FIGS. 2A and 2B, and/or the collector 300 depicted in FIG. 3.

According to embodiments, the collection container 402 may be oriented such that an axis of symmetry (not shown) extending from the first end 404 to the second end 408 is oriented at least approximately in a direction 418 of gravitational settling of a particle 420. A flow device (e.g., the fluid device 120 depicted in FIG. 1) may be configured to provide a fluid flow in a direction 422 at least approximately opposite the direction 418 of gravitational settling of the particle 420. Although only one particle 420 is depicted in FIG. 4, it should be understood that the principles and operations discussed herein with reference to FIG. 4 may be equally applicable to any number of particles. The particle 420 may, in embodiments, be an aerosol particle having an aerodynamic diameter of at least about 10 µm. In embodiments, the aerodynamic diameter of the particle 420 may be within a range of about 10 µm to about 100 µm. In embodiments, the aerodynamic diameter of the particle 420 may be less than about 10 µm or more than about 100 µm.

As illustrated in FIG. 4, the system 400 includes a number of particle detectors. In embodiments, the system 400 may include any one or more of the illustrated particle detectors, in any number of different combinations, orientations, and/or the like. As shown, the illustrated embodiments include a Mie scattering particle counting system 424. The Mie scattering particle counting system 424 includes a Mie scattering laser generator 426 operatively coupled to the collection container 402 and configured to provide a Mie scattering laser sheet 428 in the collection chamber 414. The Mie scattering laser generator 426 may include, for example, a Mie scattering laser 430 and a set of optics 432 configured to form, from a Mie scattering laser beam 434 produced by the Mie scattering laser 430, the Mie scattering laser sheet 428. A Mie scattering photodetector 436 is operatively coupled to the collection container 402 and is configured to produce a signal in response to detecting light 438 scattered off of the particle 420 when the particle 420 intersects the Mie scattering laser sheet 428. In embodiments, the Mie scattering photodetector 436 and/or a controller (e.g., the controller 130 depicted in FIG. 1) is configured to determine whether the signal exceeds a threshold, and register a count if the signal exceeds the threshold.

The system 400 depicted in FIG. 4 also includes a trigger laser system 440. The trigger laser system 440 includes a trigger laser generator 442 operatively coupled to the collection container 402 and configured to provide a trigger laser beam 444 within the collection chamber 414. The trigger laser generator 442 may include, for example, a trigger laser 446 and a set of trigger laser focusing optics 448 configured to focus the trigger laser beam 444. In embodiments, the trigger laser focusing optics 448 may be configured to create a focal point 450 within the collection chamber 414. The trigger laser system 440 also includes a trigger photodetector 452 operatively coupled to the collection container 402 and configured to detect at least one of an interruption of the trigger laser beam 444 by the particle 420 and Mie-scattered light produced when the particle 420 passes through the trigger laser beam 444.

As shown in FIG. 4, the system 400 further includes a laser induced breakdown spectroscopy (LIBS) system 454. The LIBS system 454 includes a LIBS laser generator 456 operatively coupled to the collection container 402 and configured to provide a LIBS laser beam 458 that produces a plasma 460 within the collection chamber 414. The LIBS laser generator 456 may include, for example, a LIBS laser 462 that produces the LIBS laser beam 458 and a set of LIBS focusing/collecting optics 464 that are configured to focus the LIBS laser beam 458 and to collect an optical emission 466 produced by the plasma 460 when the particle 420 passes through the plasma 460. The LIBS laser generator 456 may also include beam/return separation optics 468 configured to keep the LIBS laser beam 458 separate from the collected optical emission 466. A LIBS spectrometer 470 is operatively coupled to the collection container 402 and configured to receive the optical emission 466, via signal relay optics that may include, for example, a fiber couple 472 and an optical fiber 474. The LIBS spectrometer 470 may be configured to determine, based on the optical emission 466, a composition of the particle 420.

According to embodiments, as indicated above, the particle detector of the system 400 may include any combination of the laser systems 424, 440, and 454 described above. Embodiments of the various illustrated components may be coupled to the collection container 402 using any number of different techniques, mechanisms, and/or the like. Additionally, the collection container 402 may include any number of windows 476 configured to facilitate providing laser beams, sheets, and/or the like to the collection chamber 414 and/or to receive scattered light, laser beams, and/or the like from the collection chamber 414. Any one or more of the windows 476 may include apertures, transparent portions of the collection container wall 410, and/or the like. In embodiments, the entire collection container wall 410 may be transparent, partially transparent, opaque, and/or the like. In other embodiments, only a portion (e.g., a portion corresponding to the measurement region 416) of the collection container wall 410 may be transparent, partially transparent, opaque, and/or the like.

In embodiments, for example, the system may include all of the illustrated systems 424, 440, and 454, which may, in embodiments, work at least somewhat in concert. An example of a process that may be implemented using embodiments of the system 400 is described below. It should be understood that this exemplary process is simply one example of any number of different processes that may be implemented in accordance with embodiments of the system 400, and is not intended to limit the scope of the disclosed subject matter, but, rather, is presented only for purposes of clarifying aspects of embodiments of the disclosure.

In the exemplary process, the Mie scattering particle counting system 424 and the LIBS system 454 measure aerosol particles 420 falling through the collection container 402. A vertical flow 422 of fluid restricts the size (aerodynamic diameter) of aerosol particles 420 which are able to enter a measurement region 416 within the collection chamber 414 of the collection container 402. Once inside, for example, a particle 420 falls downward against the fluid flow 422 and intersects a Mie scattering laser sheet 428 provided by a Mie scattering laser generator 426. Laser light 438 is Mie scattered off of the particle 420 and collected by a photodetector 436. If the Mie scattering signal exceeds a particular threshold, then the signal may be interpreted as being due to a particle 420 and a count may be registered (e.g., by the photodetector 436, a controller, and/or the like).

In the exemplary process, the particle 420 continues to fall downward and may intersect a trigger laser beam 444. The trigger laser beam 444 may be provided by a trigger laser generator 442, which may include trigger laser focusing optics 448 configured to focus the trigger laser beam 444 to a focal point 450 within the measurement region 416. When the particle 420 intersects the trigger laser beam 444, a negative pulse may be observed on a trigger laser photodetector 452. When a negative pulse (e.g., a trigger signal) is detected, a LIBS measurement may be initiated (e.g., by the LIBS system 454, a controller, and/or the like).

The LIBS system includes a LIBS laser generator 456 that provides a pulsed laser beam 458, directed through beam/return separation optics 468 and focused by focusing/collecting optics (e.g., a lens) 464 to a point within the measurement region 416. The LIBS laser pulse may be time delayed, based on the particle 420 time-of-flight between the Mie laser sheet 428 and the trigger laser beam 444, such that the LIBS laser focal point intersects, or nearly intersects, the particle 420. A plasma 460 is produced by the LIBS laser beam 458, which vaporizes and excites atoms in the aerosol particle, which may be caused to fluoresce. The optical emission 466 from the plasma 460 is collected by the focusing/collecting optics 464, separated from the laser beam 458 by beam/return separation optics 468 and redirected to a spectrometer 470 via relay optics, which may include a fiber couple 472 and a fiber optic cable 474. The measured spectrum of the plasma emission 466 may be used to determine a composition of the particle 420.

The illustrative system 400 shown in FIG. 4 is not intended to suggest any limitation as to the scope of use or functionality of embodiments of the present disclosure. Neither should the illustrative system 400 be interpreted as having any dependency or requirement related to any single component or combination of components illustrated therein. Additionally, various components depicted in FIG. 4 may be, in embodiments, integrated with various ones of the other components depicted therein (and/or components not illustrated), all of which are considered to be within the ambit of the present disclosure.

Figure 5:
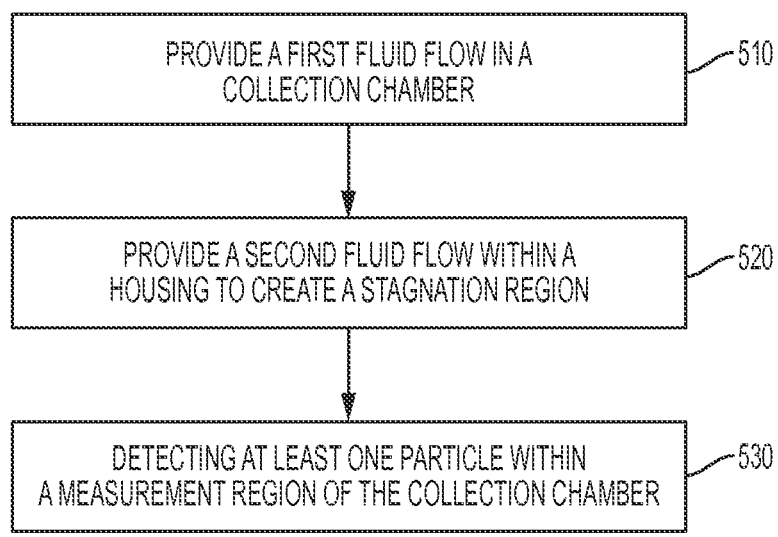
FIG. 5 is a flow diagram depicting a method for characterizing particles in an aerosol, in accordance with embodiments of the present disclosure.

Embodiments of systems for characterizing particles in an aerosol have been described above. FIG. 5 is a flow diagram depicting a method 500 for characterizing particles in an aerosol, in accordance with embodiments of the disclosed subject matter. According to embodiments, aspects of embodiments of the method 500 may be performed by, and/or using, embodiments of systems described herein such as, for example, the system 100 depicted in FIG. 1, the collection container 200 depicted in FIGS. 2A and 2B, the collection container 300 depicted in FIG. 3, and/or the system 400 depicted in FIG. 4. Embodiments of the method 500 include providing a first fluid flow in a collection chamber defined within a collection container (block 510). The collection container may include a first end having an opening, a second end, and a collection container wall extending between the first end and the second end. The first fluid flow may be provided in a direction from the second end toward the first end.

In embodiments, the method 500 further includes providing a second fluid flow within a housing (block 520). In embodiments, at least a portion of the collection container is disposed within the housing. The housing may include a first housing end having a cap disposed above, and spaced apart from, the first end of the collection container. The cap may include an inlet aperture defined therein, which may be positioned over the opening in the first end of the collection container. The housing may also include a second housing end; and a housing wall extending downward from the first housing end such that at least a portion of the housing wall is positioned external to, and spaced apart from, the collection container wall, thereby forming a gap between an outside surface of the collection container wall and an inside surface of the housing wall. According to embodiments, the second fluid flow is provided in a direction away from the first housing end, thereby creating a fluid stagnation region above the first end of the collection container.

Embodiments of the method 500 include detecting at least one particle within a measurement region of the collection chamber (block 530). According to embodiments, detecting the at least one particle within the measurement region of the collection chamber includes providing a laser induced breakdown spectroscopy (LIBS) laser beam within the collection chamber, where the LIBS laser beam produces a plasma within the collection chamber such that the produced plasma causes an optical emission when the at least one particle passes through the plasma; receiving the optical emission; and determining, based on the optical emission, a composition of the at least one particle. In embodiments, detecting the at least one particle within the measurement region of the collection chamber may include providing at least one of a trigger laser beam and a Mie scattering laser sheet within the collection chamber; detecting Mie-scattered light; and detecting, based on the Mie-scattered light, the at least one particle.

Example

Figure 6A:
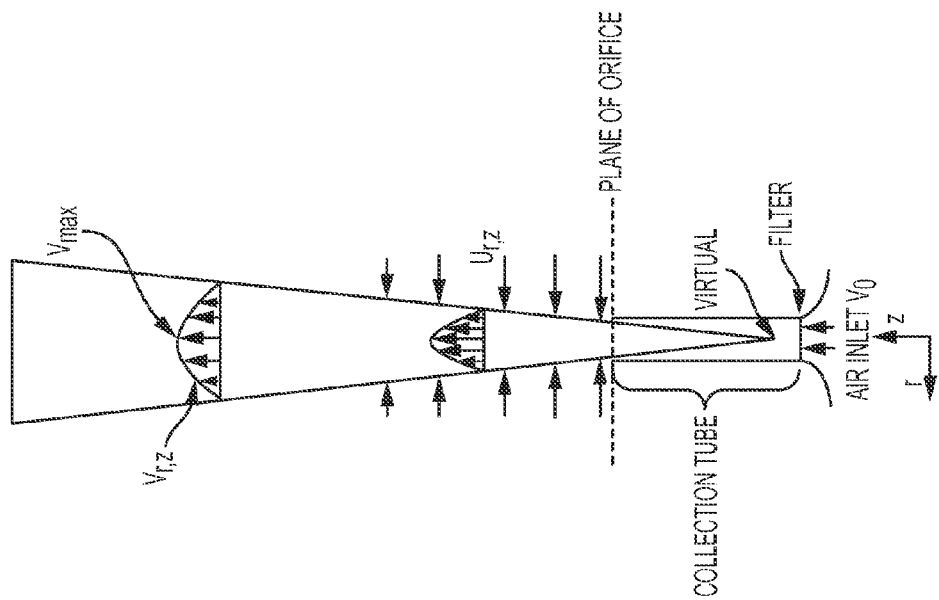
FIGS. 6A and 6B are schematic diagrams of a collection container, in accordance with embodiments of the present disclosure.
Figure 6B:
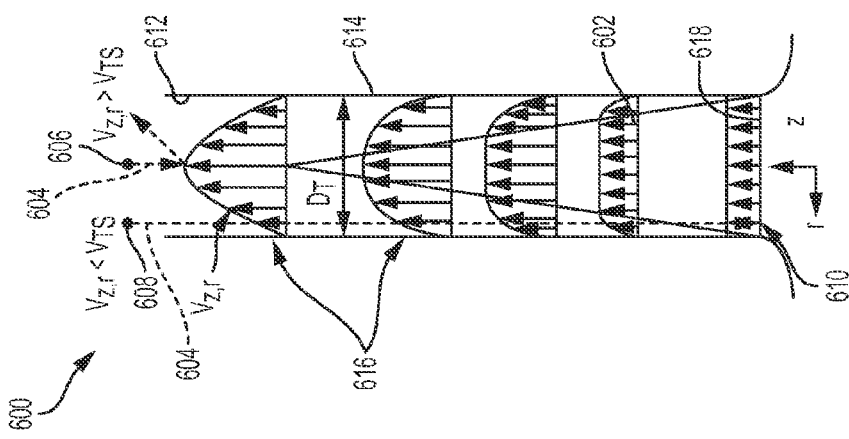
Figure 7B:
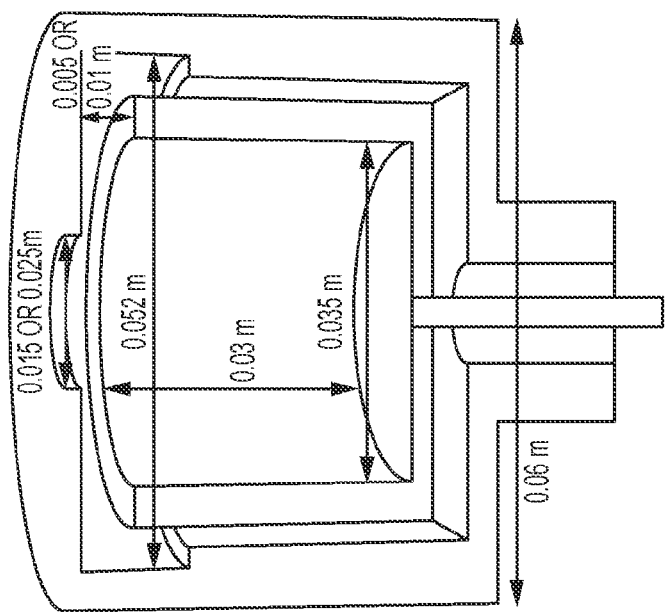
FIGS. 7A and 7B are cross-sectional schematic diagrams of another collection container, in accordance with embodiments of the present disclosure.
Figure 7A:
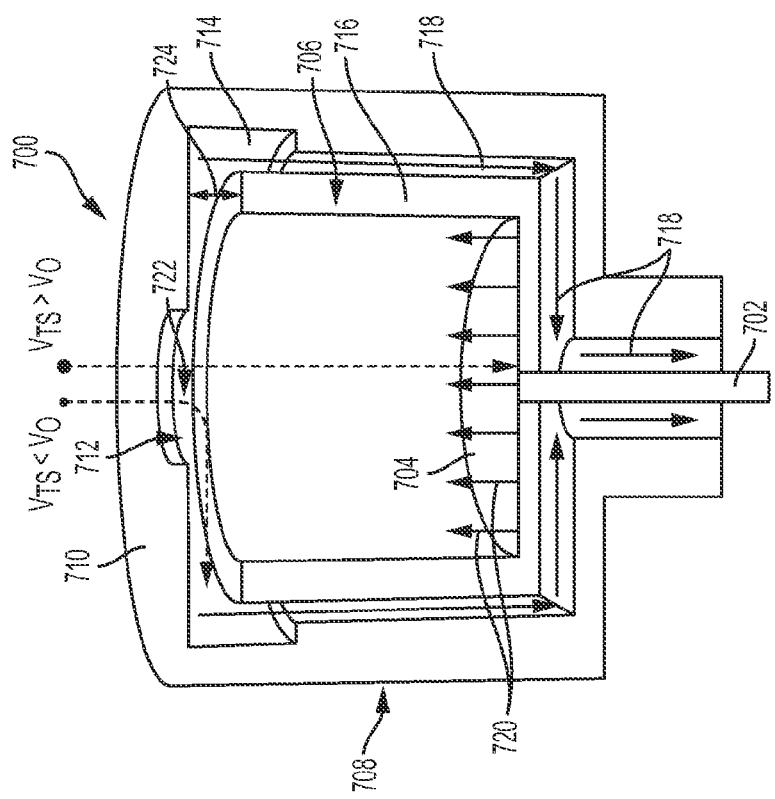

A schematic diagram of a collection container 600, in accordance with embodiments of the disclosure, is shown in FIG. 6A. The operation of the collection container 600 is based on the principles of a vertical elutriator. In the Stokes drag region, the terminal settling velocity of a particle, $V_{TS}$, occurs when the upward drag on the particle equals the downward force of gravity, $$V_{TS} = \frac{d_p^2 \rho_p C_c g}{18\mu}, \quad (2)$$

where $d_p$ is particle diameter, $\rho_p$ is particle density, $C_c$ is the slip correction factor, g is the acceleration due to gravity, and $\mu$ is fluid viscosity (Hinds 1999).

For particle settling outside the Stokes region, where particle Reynolds number ($Re_p$) is greater than unity, Eq. (2) loses accuracy. Instead, an alternative equation accurate within 3% for $1<Re_p<600$, can be used (Hinds 1999), $$V_{TS} = \left(\frac{\mu}{\rho_g d_p}\right) \exp(-3.070 + 0.9935J - 0.0178J^2) \quad (3)$$

where $$J = \ln\left(\frac{4\rho_p \rho_g d_p^3 g}{3\mu^3}\right) \quad (4)$$

and $\rho_g$ is the gas density. For spherical particles settling in air at normal conditions, non-Stokes settling occurs for particles larger than approximately 80 μm in aerodynamic diameter.

Embodiments of systems for characterizing particles described herein operate by directing filtered fluid (e.g., gas) upwards (vertically) through an open collection container 600, in a direction 602 opposite that of a direction 604 of gravitational settling of a particle 606, 608. If the upward fluid flow velocity in the collection container 600 is less than the terminal settling velocity of the particle 606, 608, then the particle 606, 608 should settle down through the collection container into a measurement region, which, in embodiments, includes a filter 610 disposed at a lower end of the collection container upon which the particle 606, 608 deposits. If the upward fluid flow velocity is higher than the terminal settling velocity of the particle 606, 608, then the particle 606, 608 should be blown upward and out of the collection container 600. Thus, the upward velocity can be varied in the collection container 600 to select a minimum particle size (aerodynamic diameter) that will settle to the measurement region. In this Example 1, collection tube velocities were chosen to equal the terminal settling velocity of particles with aerodynamic diameters of 30, 40, 50, 60, 70, and 80 µm.

Ideally, a collector would provide a sharp cut; that is, no particles smaller than the cut size, for which the particle's terminal settling velocity equals the upward air velocity in the collection container, would be collected at all. Furthermore, all particles larger than the cut size would be collected completely. In this case, the cutoff curve, a plot of collection efficiency against particle aerodynamic diameter, would increase from zero to unity at the particle cut size.

Analytical models and computational fluid dynamics (CFD) simulations were used to predict the performance of two collectors. The first collector (referred to, alternatively, as the Portable Inhalable Particle Separator (PIPS)) was similar to the collector 200 described in FIGS. 2A and 2B, having a collection container with no housing, as described herein; and the second collector (referred to, alternatively, as the PIPSv2) was similar to the collector described in FIG. 3, having a collection container at least partially disposed within a housing. The collection container of each of the two containers was cylindrical and, as such, may be referred to herein, interchangeably, as a "collection container" or a "tube." Sampling efficiencies of these collectors were tested in a calm-air chamber with polydisperse, fluorescent microspheres (10 to 100 µm). Epifluorescent microscopy of settled dust was used to determine reference particle counts and sizes. Both devices are capable of size-selective sampling; however, the second collector produced higher sampling efficiencies and sharper cutpoints compared to the simpler elutriator design of the first collector. Experimental sampling efficiencies for both collectors showed good agreement with computational and analytical solutions. This work suggests, for example, that these devices can size-segregate inhalable aerosols in quiescent environments.

Air Flow in the First Collection Container

As illustrated in FIG. 6A, at the base of the first collection container 600, where the filter 610 is located at the bottom of the collection container 600, air exiting the filter 610 is assumed to have a uniform upward velocity, $V_0$. As air flows upward through the collection container 600, its velocity along the inside surface 612 of the container wall 614 of the collection container 600 is reduced by friction. As the air velocity within this viscous boundary layer is reduced, conservation of momentum increases the velocity within the inviscid core (i.e., the centerline flow outside the boundary layer); for laminar flow, these phenomena produce a parabolic velocity profile 616, as shown in FIG. 6A. For fully-developed laminar flow in a tube, the average velocity is approximately half of the velocity at the centerline. This parabolic profile will cease changing shape after a certain length, known as the entrance length, Le, given by (Fargie and Martin 1971):

$$L_e \approx 0.06 D_T Re_f \quad (5)$$

where $Re_f$ is the fluid Reynolds number and $D_T$ is the diameter of the tube. Beyond $L_e$ the inviscid core disappears and the fully-developed flow maintains the same parabolic shape downstream.

The fluid flow inside the first collection container 600 presents several challenges in the prediction of particle trajectories and collection. First, a non-uniform velocity profile at the top of the collection container 600 and beyond may affect particle trajectory toward the container 600. Second, once particles are in the container 600, the developing flow profile 616 and corresponding velocity magnitudes, which change as a function of depth, may affect particle collection. Thus, particles that penetrate past the inlet of the sampler still may not reach the measurement region (in this case, a filter 610 located at the base of the container 600). If air at the top of the collection container 600 has a parabolic velocity profile, then a particle with aerodynamic diameter equal to the cut size that falls towards the container 600 could enter the container 600 or be blown out, depending on its initial radial position (FIG. 6A). Consider a 50 µm particle and a collector operating at a cut size of 50 µm. If the particle 608 falls relatively close to the inside surface 612 of the container wall 614, and in the region where $V_{z,r} < V_{TS}$, then the particle 608 generally will enter the collection container 600. If the particle 606 falls close to the centerline and in the region where $V_{z,r} > V_{TS}$, then the particle 606 generally will be ejected from the collection container 600. As a result, the collector would not have the desired, sharp cut at 50 µm as some particles smaller than the cut size could enter but some particles larger than the cut size could be ejected.

The axial velocity profile within the collection container 600 also changes as particles approach the filter 610 at the collection container 600 bottom. Particles smaller than the cut size that enter near the wall 614 will encounter air with higher upward velocity as they approach the filter 610. Thus, the tendency for a velocity profile to allow particles smaller than the cut size to enter the collection container 600 near its wall 614 is generally self-correcting, as these particles should generally not reach the filter 610 (where velocity, $V_0$, is uniform across the filter 610 face 618). On the other hand, particles larger than the cut size that fall near the container 600 centerline generally will be ejected and not be sampled. Collection should be low, as intended, for particles smaller than the cut size, but incomplete for particles larger than the cut size. A more pronounced velocity profile should cause a more gradual increase in collection efficiency with size.

The entrance length, Le, at the top of the first collection container 600 was calculated for each cut point from Eq. (5). The percent of developed flow at the top of the collection container 600 was calculated by taking the ratio of the container length to the entrance length (Table 1, below). Because the collection containers used in this experiment were only a small fraction of Le, the effect of velocity profile on particle sampling should be small.

TABLE 1

| Particle Cut Size, µm | PIPS filter velocity, m s$^{-1}$ | Entrance Length, m | % developed flow |
|---|---|---|---|
| 30 | 0.027 | 0.111 | 13 |
| 40 | 0.048 | 0.197 | 7.6 |

TABLE 1-continued

| Particle Cut Size, μm | PIPS filter velocity, m s$^{-1}$ | Entrance Length, m | % developed flow |
|---|---|---|---|
| 50 | 0.075 | 0.307 | 4.9 |
| 60 | 0.108 | 0.440 | 3.6 |
| 70 | 0.148 | 0.570 | 2.6 |
| 80 | 0.193 | 0.709 | 2.1 |

Analytical Flow Solution and Sampling Efficiency

The Reynolds numbers associated with air flow through the first collection container are very low, from 60 to 370 for particle cut sizes from 30 to 80 μm, so that the air flowing out from the collection container forms a dissipated laminar jet (McNaughton and Sinclair 1966; Reynolds 1962). Under these conditions the jet projects without mixing a certain distance into the still air, then disperses laterally. Analytical methods to describe jet flow at these low Reynolds numbers are not available. Although jet flow does not become fully turbulent until Reynolds number exceeds about 3000, equations for the propagation of a turbulent jet (Schlichting et al. 2000) were used here with the understanding that, at best, they give a rough approximation to actual flow conditions.

As a turbulent air jet enters quiescent air, a velocity shear is created between the jet and the air causing turbulence and mixing. The jet gradually expands, its upward velocity decreases, as depicted in FIG. 6B, and it entrains some surrounding air. The radius of the jet is proportional to the distance downstream from the discharge location (Schlichting et al. 2000).

Calculated Velocity Profile

Schlichting's boundary theory (Schlichting et al. 2000) defines the characteristics of turbulent jets. The axial velocity profile is described by $$\frac{V_{z,r}}{V_{max}} = e^{-94(r/z)^2} \tag{6}$$

and the centerline velocity by $$V_{max} = 12\frac{D_T}{2z}V_o. \tag{7}$$

Combining equations 6 and 7 gives $$V_{z,r} = 12\frac{D_T}{2z}V_o e^{-94(r/z)^2} \tag{8}$$

which allows the axial velocity profile to be solved as a function of axial distance from the jet origin, z, and radial distance from the jet centerline, r.

The initial radius of the jet that comes from the top of the collection container is the radius of the container. The equations of turbulent jet spreading are solved from a single point for the jet origin, called the virtual origin, located inside the container where z=0, and set as the axial distance where the axial velocity at the edge of the container is half that at the centerline (Schlichting et al., 2000).

Radial air velocity was calculated using (Bird et al. 2007)

$$U_{z,r} = \frac{\left(\frac{Cv^*}{z}\right)\left(\frac{Cr}{z}\right) - 0.25\left(\left(\frac{Cr}{z}\right)^3\right)}{\left(1 + 0.25\left(C\frac{r}{z}\right)^2\right)^2} \tag{9}$$

where C is a dimensionless integration constant (15.1), v* is the turbulent kinematic viscosity given by (Bird et al. 2007)

$$v^* = \frac{\left(\frac{3}{16}\right)^{0.5} V_o \frac{D_T}{2}}{C} \tag{10}$$

Axial and radial air velocities were solved for turbulent jets for the upward flow velocities defined in Table 1, above.

Calculated Particle Trajectories

Particle trajectories approaching the first collection container were calculated using the particle terminal settling velocity (equations (3) and (4)) and jet velocities (equations (8)-(10)). The initial particle release height was 100 cm above the jet at specified radial positions. The upward and radial velocities for the jet at the initial release position were calculated. The particle's axial velocity was estimated as a function of time and location by subtracting the axial jet velocity from the particle's terminal settling velocity. The particle's axial velocity times a nominal time step (0.05 seconds) was then subtracted from the initial axial position to compute the new axial position. The particle radial position was then updated using the initial radial distance plus the outward radial velocity times the time step. The particle's axial and radial positions were calculated until the particle's axial position was below the top of the first collection container. At that axial position the particle's radial position was compared to the location of the container wall. The initial radial particle release position was varied until the particle's final radial position was just inside the container wall. Collection efficiency of the first collector was then calculated using $$E = \left(\frac{x_p}{\frac{D_T}{2}}\right)^2 \tag{11}$$

where $x_p$ is the initial radial particle release location and $D_T/2$ is the radius of the collection container.

Design Concept for Jet-Free PIPS (PIPSv2)

As discussed above, jet effects at the air outlet (particle inlet) at the top of the first collection container could affect particle sampling efficiency. To reduce such problems, a second collector design, as described above, was developed to create a stagnation point directly above the inlet of the upward-facing collection container.

FIGS. 7A and 7B include two cross-sectional schematic diagrams of the second collector 700 showing flow paths and relevant dimensions, respectively. As in the design of the first collector, clean air, provided via a conduit 702, flows upwards through a filter 704 and into a collection container 706. However, the second collector 700 also includes a housing 708 having a cap 710 with a round inlet aperture 712 that is centered directly above the collection container 706. Below this cap 710, air coming from the collection container 706 is pulled radially outward into an annular space 714 between the housing 708 and container wall 716, and from there out the bottom of the collector 700. This exhaust flow 718 is set to equal the upward flow 720 through the collection container 706 so that no air enters the collector 700 through the cap inlet aperture 712. As the upward flow 720 from the collection container 706 bends radially outward, it forms an axial stagnation point 722 below the cap inlet aperture 712. From this stagnation point 722, smaller particles that fall through the cap inlet aperture 712 are carried away with the radial, outward flow 718 whereas larger particles fall into the collection container 706. This design reduces, and/or eliminates, the jet that emanates from the top of the collection container 706 and should improve the sharpness of the resultant cutoff curve.

The separation distance, defined as the gap 724 between the bottom of the inlet cap 710 and the top of the collection container 706, was varied to determine its effect on the cutoff curve. Two separation distances were investigated: 5 and 10 mm. The diameter of the inlet aperture 712 in the cap 710 was varied as well (15, 20, 35 mm).

Computational Fluid Dynamics (CFD) Modeling of PIPS and PIPSv2

CFD modeling was conducted to investigate air flow, particle transport, and sampling efficiencies for the first and second collectors operating in calm air. Ansys software (Design Modeler, Meshing application, and Fluent 14.0, Ansys Lebanon, N.H., USA) was used to create the geometry, generate the mesh, and solve the equations of fluid flow. Steady-state, incompressible Navier-Stokes equations were used to model flow. Once the fluid flows were solved and the quality of the solution assessed, laminar particle trajectories were simulated to determine sampler efficiency. Six cut sizes were investigated: 30, 40, 50, 60, 70, and 80 μm (TABLE 1, above). The first collector was modeled as a tube with an inner diameter of 0.032 m, an outer diameter of 0.037 m and 0.015 m high. The second collector was modeled as an interior collection tube with an inner diameter of 0.035 m, an outer diameter of 0.037 m and 0.030 m high. The cap had an inside diameter of 0.052 m and outer diameter of 0.060 m. Six sampler geometries were investigated for the second collector: three cap inlet openings and two separation distances (TABLE 2, below). The effect of sampler geometry on efficiency was investigated for the 50 μm cut size. Both collectors were modeled 0.254 m above the floor in the center of a calm-air chamber with dimensions of 1 m×1 m×1 m. Simulated collector efficiency was calculated by taking the ratio of the upstream area where particles were aspirated to the cross-sectional area of the collection tube and filter, analogous to Eq. (11) above.

TABLE 2

| Sampler | Inlet Opening, m | Separation Distance, m | Cut Sizes |
|---|---|---|---|
| PIPS | 0.032 | NA | 30, 40, 50, 60, 70, 80 μm |
| PIPSv2 | 0.015 | 0.005 0.010 | 30, 40, 50, 60, 70, 80 μm |
|  | 0.020 | 0.005 0.010 | 30, 40, 50, 60, 70, 80 μm |
|  | 0.035 | 0.005 0.010 | 50 μm |

Sampler Fabrication and Design

Figure 8A:
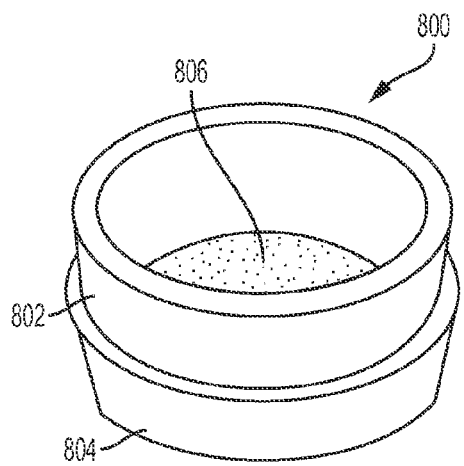
FIG. 8A is a perspective view of a collector, in accordance with embodiments of the present disclosure.

The first collector 800 (FIG. 8A) utilized a vertical collection tube 802 having an inner diameter (ID) of 32 mm and a length of 15 mm, with its base fitted into a 37-mm filter cassette 804. A short tube length was selected so that the effects of non-uniform axial velocities on particle sampling efficiency (i.e., a parabolic laminar flow profile) were minimized within the tube. The first collection tube 802 was made from aluminum to minimize electrostatic effects. An O-ring (not shown) was situated at the base of the collection tube 802 to provide sealing between the tube 802 and the filter cassette 804. A coarse filter 806 (Cellulose Support Pad, Pall) was chosen because of its rigidity under positive pressure (via upward air flow). A rubber plug (not shown) with a hose-barb fitting was placed over the top of the collection tube 802 to calibrate airflow through the first collector 800.

Figure 8B:
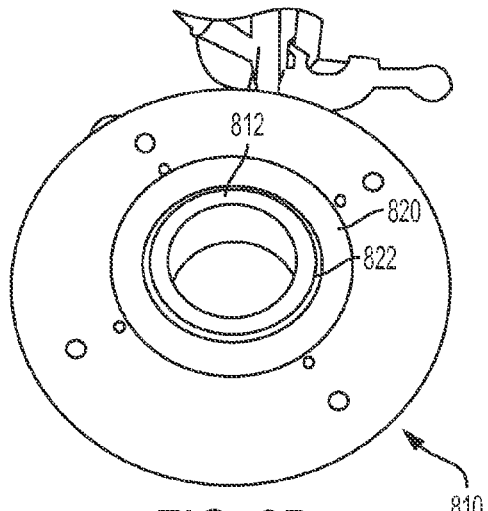
FIGS. 8B-8D are perspective views of another collector, in accordance with embodiments of the present disclosure.
Figure 8C:
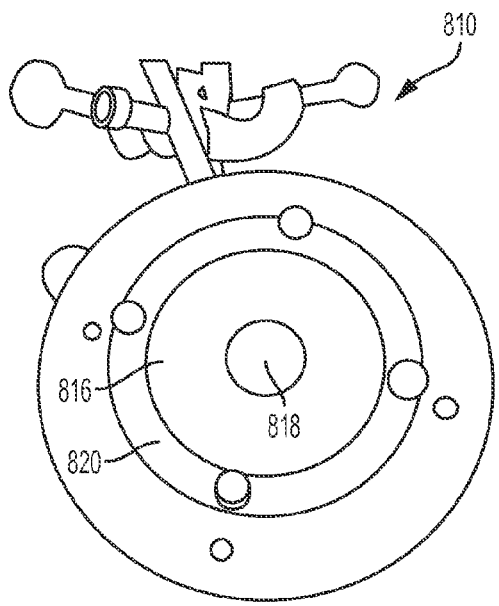
Figure 8D:
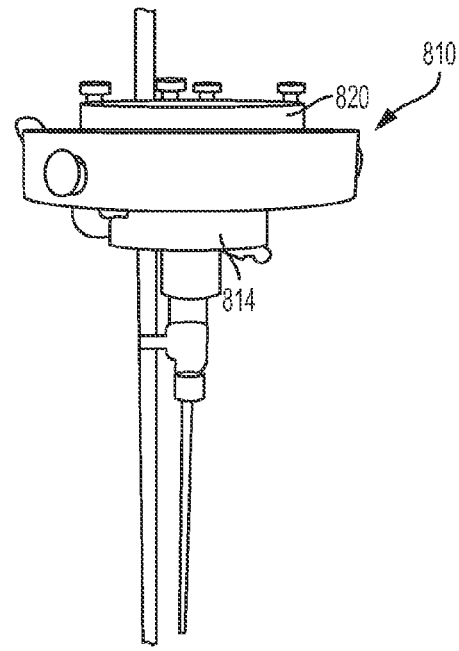

The second collector 810 (FIGS. 8B, 8C, and 8D) had a vertical collection tube 812 that was 30 mm long with an inner diameter (ID) of 35 mm and an outer diameter (OD) of 37 mm, which also allowed a 37 mm filter and cassette 814 to be attached to its bottom. Cap 816 openings 818 of 15 and 20 mm, and separation distances between the bottom of the cap 816 and the top of the collection tube 812 of 5 and 10 mm, were investigated to inform the optimal settings for a sharp cutoff (FIG. 8C). The outer housing 820 had an ID and an OD of 40 and 42 mm, respectively, and was configured to form a gap 822 between the outer housing 820 and the collection tube 812 through which the exhaust flows were pulled. The second collector 810 was made from aluminum for durability and to minimize electrostatic effects, and weighed approximately 750 g. Two rotary vane pumps (GAST rotary vane oil vacuum pump, model 0323) (not shown) provided the necessary airflows; each was controlled by a separate needle valve. Calibrated rotameters monitored flows during a given test and were adjusted as necessary to ensure balanced flow. If the flow varied more than 10% over the test, then the test was considered invalid and repeated.

Test Chamber

Figure 9:
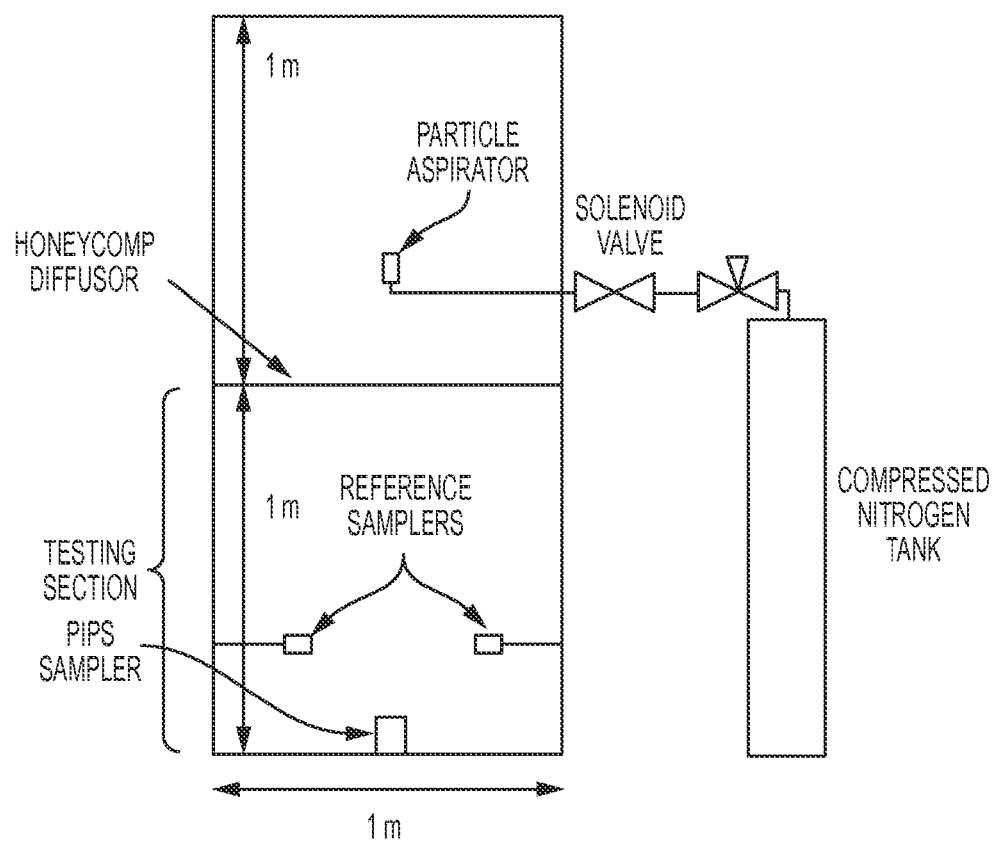
FIG. 9 is a schematic diagram of a testing environment, in accordance with embodiments of the present disclosure.

A vertical, calm-air chamber (2.5 m high with 1×1 m cross-section) was used to investigate the collection efficiency of the samplers (FIG. 9). The aerosol dispersion system, located in the upper section of the chamber, was comprised of a cap holding 0.1 g of test powder connected to a compressed nitrogen source. A solenoid valve was attached to the compressed nitrogen line. When the valve was opened, a jet of nitrogen ejected the test powder into the chamber. The nitrogen jet was activated once, for fewer than 5 seconds, to aerosolize the test particles. A honeycomb diffusor (25 mm cell size) was located in the center of the chamber (at a height of 1.25 m) to break up any turbulent eddies generated during powder dispersion (keeping the lower half of the chamber relatively quiescent). The aerosol was then allowed to settle for 10 minutes, sufficient for the smallest particles of interest to reach the base of the chamber.

Three reference samplers and either the first collector or second collector were located in a square pattern centered in the middle of the chamber floor. The reference samplers were open, 37-mm cassettes holding filters like the one used in the first collector or second collector. They were located 250 mm above the chamber floor, above the inlet of the first collector or second collector, to minimize the influence of jet effects or particles ejected from the first collector or second collector during measurements. After each powder injection the filters in the reference and test samplers were changed, and the first collector or second collector rotated to a different corner of the square. This process was repeated until four tests were made, one with the first collector or second collector in each corner of the square pattern. This set of four tests comprised one experiment.

Figure 10:
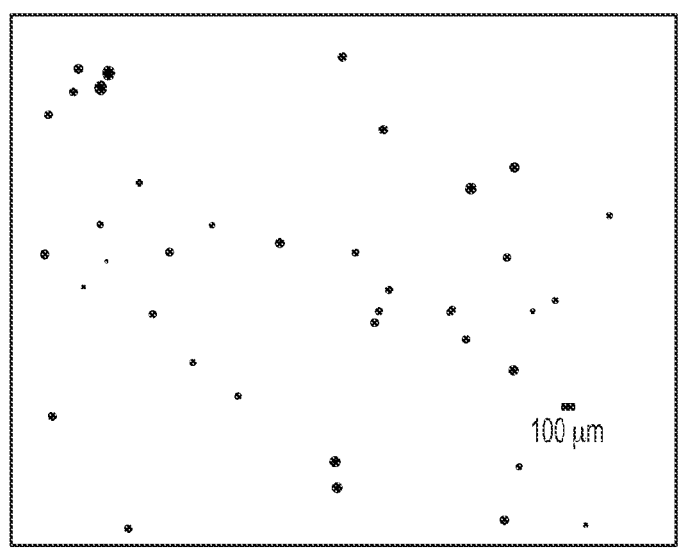
FIG. 10 depicts a particle distribution collected by a sampler, in accordance with embodiments of the present disclosure.

The polydisperse test powder was fluorescent, polyethylene microspheres of unit density with sizes ranging from 10 to 90 µm (UVYGPMS, Cospheric LLC). An epi-fluorescent microscope (Orthoplan, Leica) and fluorescence filters (Vivid Plus Set XF05-2/B, Omega Optical) were used to image collected particles. Filters were imaged under a 1.6× objective lens and a 10× objective eyepiece. ImageJ software (NIH, V1.46r (Rasband)) was used to obtain the area of each particle, from which the corresponding particle aerodynamic diameters were calculated using Microsoft Excel. A stage micrometer provided a reference for ImageJ size analysis. Size distributions of the reference samplers were measured using microscopic analysis following the procedure outlined above. Particles were sorted by aerodynamic diameter into one of nine size bins from 15 to 95 µm, each with a 10 µm bin width. FIG. 10 shows particles from a reference sampler photographed and analyzed using this procedure.

Deposition patterns in the chamber were assessed to ensure that particles were dispersed uniformly. The test aerosol was dispersed into the chamber, and size and count statistics generated at the four sampling locations.

Measurement of Sampling Efficiency

Three replicate experiments of four tests each were conducted for six particle size cuts (30, 40, 50, 60, 70, and 80 µm) for a total of 18 experiments per sampler. Fractional sampling efficiency ($\eta_j$) was computed for each size cut, $$\eta_j = \frac{N_{s,j}}{N_{R,j}} \tag{12}$$

where $N_{s,j}$ is the number of particles observed on the sampler filter for the jth size range and $N_{R,j}$ is the average number of particles observed on the three reference filters for the jth size.

Velocity Measurements

Velocity measurements for the 70 µm cut were taken above the first collector's collection tube to compare experimental jet velocities to those estimated by the analytical and CFD models. Jet velocity was measured using a thermal anemometer (AVM440, TSI, Shoreview, Minn., USA) directly above the center of the first collection container inlet and at distances of 10, 20, 40, and 100 mm above this location. Measurements were also taken radially from the flow axis centerline at +/−10 and +/−15 mm. Measurements were taken for 10 seconds and then averaged. This process was repeated five times at each location. Measured velocities were plotted and compared to the simulated laminar and analytical turbulent velocity profile.

Data Analysis

The spatial uniformity of test aerosol dispersed within the test chamber was assessed using ANOVA to compare the size distributions at each reference sampling location. Tukey's method of multiple comparisons was used to determine whether any locations were significantly different.

A general linear mixed model was used to compare cutoff curves of the first and second collectors. Tests of the slopes were conducted to determine if the second collector had significantly sharper cuts. Percentage difference between experimental sampling efficiency and simulated sampling efficiency was calculated for each cut point. An ANOVA was used to determine whether cap inlet diameter and separation distance had a meaningful influence on the slope of the sampling efficiency curves of the second collector.

Sampling efficiency curves for the first and second collectors were well represented by logistic functions:

$$\hat{\eta}_j = D + \frac{(A - D)}{1 + \left(\frac{d_j}{C}\right)^B} \tag{13}$$

where $\hat{\eta}_j$ is the modeled sampling efficiency for a particle with aerodynamic size j, and the coefficients A, B, C, and D were obtained by nonlinear, least-squares regression (SAS, v9.4). Table 2 lists coefficient values at all cut sizes for both the first and second collectors.

Data Inversion Procedure to Obtain Size Distribution

To determine how effectively the first and second collectors could measure the size distribution of a coarse aerosol, additional experiments were conducted with both samplers operated at each of its six cut sizes. For these experiments, only the total number of particles collected on the first or second collector filter at each cut size was measured. These data were then used to estimate the number concentration and size distribution of the test aerosol as described below, then compared with data collected simultaneously using the reference samplers.

Data inversion techniques can be used to estimate a continuous size distribution from measured particle counts in discrete bins. The simplest approach is to assume a perfectly sharp cut, then to fit a curve through a plot of the cumulative counts deposited in successive stages as a function of particle aerodynamic diameter. Typically, prior assumptions are made that the aerosol is log-normally distributed; however, many distribution curves can be fitted to the discrete data points. The sampling efficiency curves for the first collector were not sharp so that this simplistic approach was not appropriate; as a result, the following data inversion procedure was used.

A logistic function was fitted to the sampling efficiency curves for each cut point. The coefficients were obtained by nonlinear, least-squares regression. Next, an initial approximation of a count median diameter (CMD) of 52 µm and standard deviation (SD) of 15 µm were used as a random starting point; these CMD and SD values were then adjusted through a series of iterations to arrive at the optimal solution. A data-inversion spreadsheet was developed in Microsoft Excel (2010, Microsoft Corp., Seattle, Wash.) to estimate the CMD, SD, and number concentration of a normally distributed, unimodal aerosol from particle number concentrations measured with the PIPS sampler at six cutpoints following the method described by O'Shaughnessy and Raabe (O'Shaughnessy and Raabe 2003). An initial guess for the number concentration was taken as the number concentration for the 30 µm cut.

Results: Jet Velocities

For the first collector, the laminar jet profile from the CFD simulations was compared to the turbulent jet from the analytical solutions for the 70 µm cut. The centerline velocity decayed more rapidly for the turbulent analytical model compared to the simulated laminar jet. These trends compared well to published experimental observations (Labus and Symons 1972). Measured velocities decayed more rapidly at lateral distances from the first collector centerline. At increased vertical distances from the first collector, velocity decayed more rapidly than predicted by laminar jet theory.

Inspection of the CFD velocity vectors and flow streamlines showed the second collector had a flatter velocity profile than the first collector throughout its collection tube. As intended, small particles were pulled radially outward, and large particles fell into the second collector's collection tube.

Results: Spatial Uniformity of Particles in the Calm Air Chamber

Particle deposition in the test chamber was relatively uniform across the four quadrants on the chamber floor (TABLE 3, below). Location C had slightly higher particle counts than the other locations; however, variations in the size distributions between the locations were not significantly different (p=0.23).

TABLE 3

| Location | Count median diameter, µm (Std. dev.) | Number of particles (Std. dev.) |
|---|---|---|
| A | 54.9 (30.2) | 182 (22) |
| B | 63.2 (29.2) | 248 (63) |
| C | 58.2 (30.0) | 313 (64) |
| D | 62.9 (29.8) | 246 (41) |

Results: First Collector Sampling Efficiency

Figure 11:
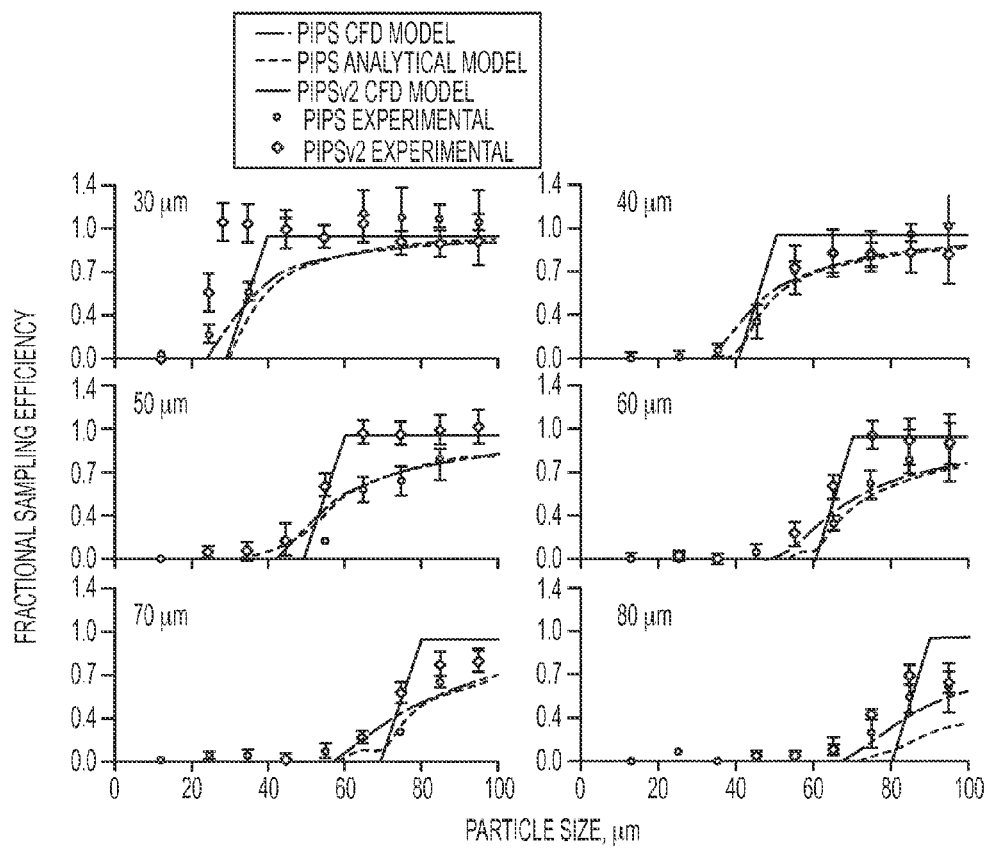
FIGS. 11, 12, 13A, and 13B are graphs depicting experimental results, in accordance with embodiments of the present disclosure.
Figure 12:
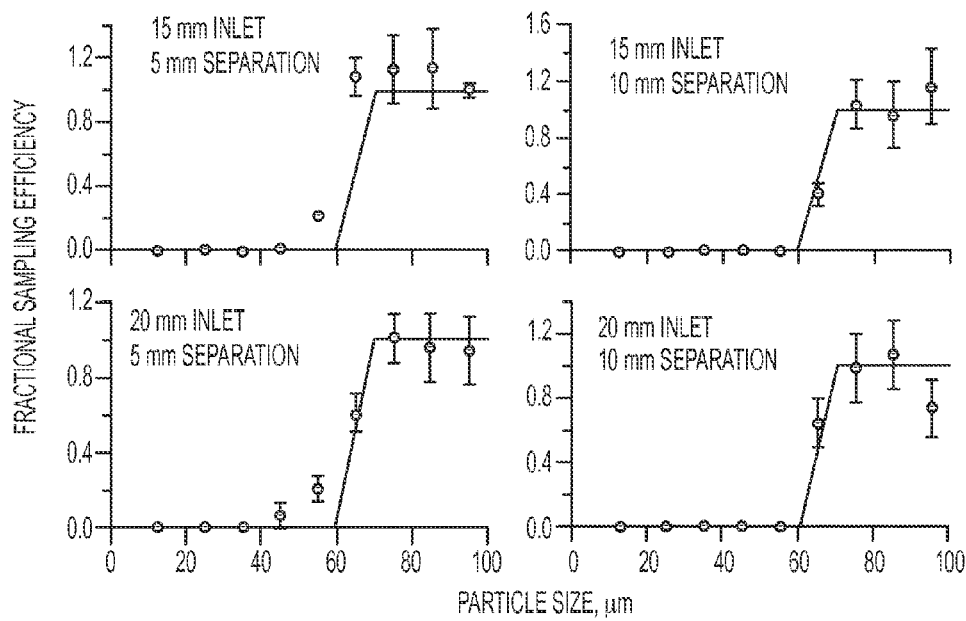
Figure 13A:
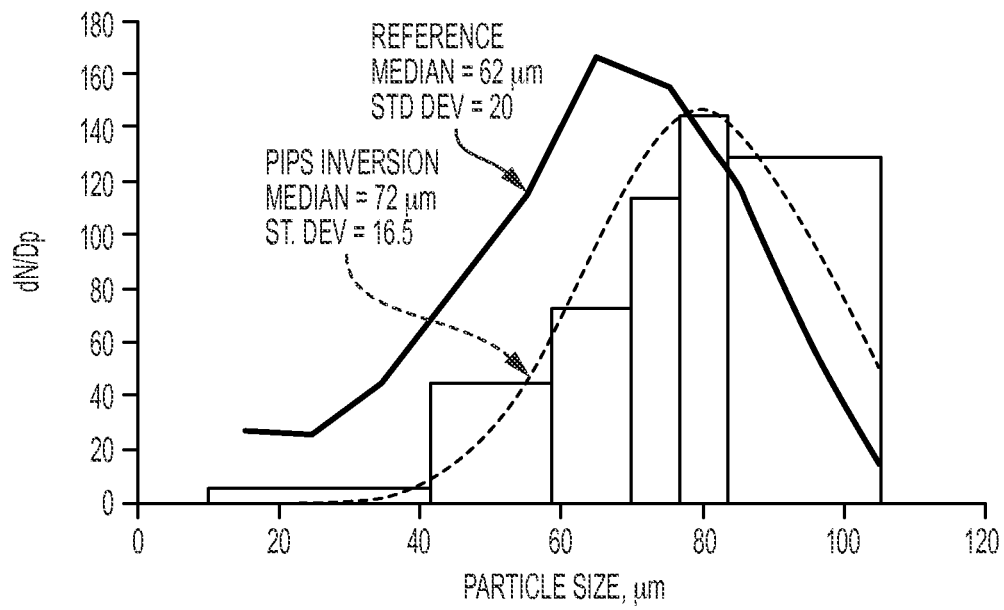
Figure 13B:
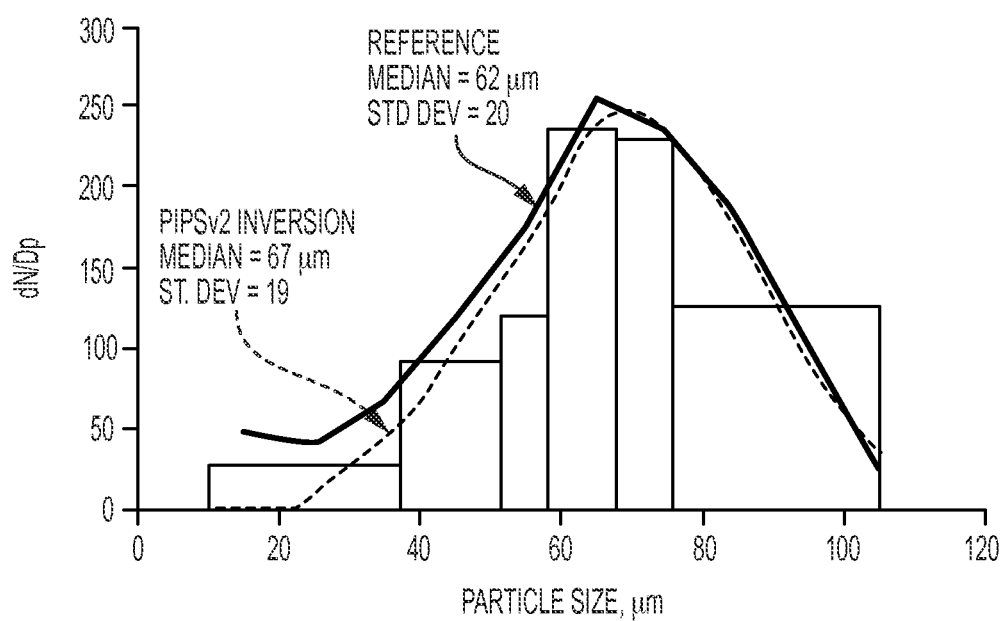

The experimental and simulated sampling efficiency curves at the six cut points for the first and second collectors are displayed in FIG. 11. In FIG. 11, CFD modeling of the second collector (20 mm inlet, 5 mm separation distance) is represented by the solid line; and CFD modeling of the first collector is represented by the dashed grey line. The experimental second collector results are represented by the solid markers and the experimental first collector results are represented by the open markers. The error bars in this figure represent one standard deviation based on the variability between sampling efficiency measurements for repeated experiments. The experimental first collector efficiency showed good agreement with the CFD model and the theoretical solution. As particle size increased, the measured first collector efficiency deviated more from the simulated sampling efficiency: the cut point became less sharp, and measured sampling efficiency for particles larger than the cut size was less than 100%. Experimental sampling efficiency was substantially higher than the simulated sampling efficiency for the 80 µm cut.

Although the first collector was predicted to perform reasonably well, particle separation curves were not as sharp as desired (FIG. 11). Analytical solutions and CFD simulations both predicted sampling efficiencies less than 100% for particles above the cut size for all cut sizes investigated. The analytical solutions predicted slightly lower sampling efficiencies than the CFD simulations, with the differences most apparent for particle sizes near the cut point. Analytical and CFD-determined efficiencies deviated most for the largest cut size, 80 µm.

Airflow in the first collector collection container that was more developed than predicted by the analytical equations could account for some lack of sharpness in the sampling efficiency curves. Velocity vectors and flow streamlines in the CFD simulations showed centerline velocities 10% higher than appropriate for the desired cut point, despite the use of a collection tube just 15 mm long.

Wall losses inside the first collector's collection tube were evaluated using CFD modeling and found to be minimal. Fewer than 5% of the incoming particles deposited on the walls for all cut sizes. Thus, in embodiments, wall deposition should not substantially affect sampling efficiency.

Results: Second Collector Sampling Efficiency

The second collector was designed to minimize the jet effect at the top of the collection tube while maintaining a flat velocity profile throughout the tube. Experimental sampling efficiency for the second collector compared reasonably well to CFD simulations. The 70 and 80 μm cuts had the greatest differences between experimental and simulated efficiencies, with experiments underestimating simulated sampling efficiencies by 20 to 30% for particles larger than the cut size. The second collector had much higher sampling efficiencies and steeper cuts than the first collector, especially for the 50 and 60 μm cut points.

The second collector's inlet openings of 15 and 20 mm resulted in sharper efficiency curves with sampling efficiencies near 100% for particles just larger than the cut point (FIG. 12). FIG. 12 illustrates the effect of inlet size and separation distance on the second collector's sampling efficiency. All test are shown for a 70 μm cut size. The error bars represent one standard deviation about repeated tests. For inlet openings of 35 mm, sampling efficiency was not as sharp. For the 35 mm inlet opening, CFD particle trajectory simulations showed particles impacting on the lip of the collection tube. Separation distances of 5 and 10 mm had little effect on the sampling efficiency, on average less than 1%. The 10 mm separation distance (for both the 15 and 20 mm inlets) resulted in slightly steeper cutoff curves and less small particle contamination. The 5 mm separation distance was less effective at preventing small particles from reaching the measurement region.

Results: Data Inversion to Obtain Size Distribution

Fluorescence microscopy of the reference sampler filters produced a count median diameter of 62 μm and a standard deviation of 20 μm (FIGS. 13A and 13B). FIG. 13A illustrates size distribution in the chamber estimated by the first collector, and FIG. 13B illustrates size distribution in the chamber estimated by the second collector. The reference size distribution was measured by optical microscopy of settled dust (the solid line in both graphs). The light grey bars represent the raw particle counts for each stage. Inversion of the first collector data resulted in a CMD of 72 μm and a standard deviation of 16.5 μm. Inversion of the second collector data resulted in a CMD of 67 μm and a standard deviation of 19 μm. Both collectors characterized the CMD and standard deviation reasonably well, although the first collector somewhat overestimated the CMD.

Results: Discussion

The sampling efficiency of the second collector was better than that of the first collector. The separation efficiency curves were sharper and overall sampling efficiency higher for the second collector. With the second collector, sampling efficiency for particles larger than the specified cut was nearly 100%, a substantial improvement over the first collector. Reasonable agreement exists between the analytical solution, CFD simulations, and experimental collection efficiencies of the first collector (FIG. 11). The CFD simulations and analytical solutions tended to slightly underestimate sampling efficiency compared to the experimental tests; however, differences in sampling efficiencies among the three methods were within 10%.

Inlet openings of 15 and 20 mm resulted in sharp cutoffs for the second collector, while the inlet opening of 35 mm resulted in sampling efficiencies similar to those found for the first collector design. Separation distance had minimal effect on sampling efficiencies. Separation distances may have been too large which could have caused removal of large particles that should have deposited on the filter. Cascade impactor theory recommends minimum jet-to-plate distance (S) to jet width (W) ratios of 1. The 15 mm inlet with 10 mm separation resulted in a S/W ratio of 0.67, which of the design parameters investigated in this study was closest to this recommended minimum. This fact could be why the 15 mm inlet and 10 mm separation resulted in the sharpest cutoff curves. Cascade impactor theory also recommends Reynolds numbers between 500 and 1000 for sharp cutoff curves. The Reynolds numbers for this study ranged from 27 to 256, well below the recommendation. Although the second collector design is quite different from that of a virtual impactor (air is not being accelerated toward an inner collection substrate), future work should take advantage of impactor theory to guide the next design iterations. Although the collection efficiencies were not as sharp or as high as desired, the second collector design did remove the presence of the jet at the top of the collection tube.

Although, in embodiments, sampling efficiency is improved with the second collector, flow control and sampler geometry are more complex. The second collector relies on balanced airflow between the air flowing up and the air pulled out. If these flows are not well-balanced, sampling efficiency could be adversely affected. Misalignment of the interior collection tube and the outer cup could create a flow imbalance across the top of the collection tube and affect the cutoff curves.

Upward flow from the first collector's collection tube was modeled as a turbulent jet for the analytical work, but laminar for the CFD work. Despite the differences in these models, the sampling efficiency curves showed good agreement. Although airflow within the first collector's collection tube compared well with theory for laminar flow, flow in the jet outside the tube was higher. The higher centerline velocity and radial spreading of the jet can help account for the gradual increase in sampling efficiency for the first collector.

If particles smaller than the cut size enter the collection container near its wall, they may be able to penetrate into the container but may not reach the measurement region. These particles may hover in the container until they either deposit on the wall or travel radially into the center region of higher velocity where they will subsequently be blown out. Particles with terminal settling velocities near the cut point may penetrate into the container but then hover above the measurement region (e.g., filter). As larger particles fall through the container, they may impact the hovering particles and remove them from the airstream. Particles hovering above the filter may also agglomerate and then deposit on the filter. Both of these phenomena would result in particles smaller than the cut size penetrating to the measurement region. The air velocity along the edges of the first collector's collection tube is slower than along the centerline, due to viscous drag along the walls. If particles enter the collection container near the walls (within the viscous boundary layer), particles smaller than the specified cut point may penetrate past the inlet and into the collection container. As these particles descend, they eventually reach a point where the viscous boundary layer is not sufficiently developed; eventually the particle's terminal settling velocity is matched by the (developing) upward flow velocity. These particles theoretically "hover" in the collection container until they either deposit on the wall, travel radially into a region of higher velocity where they are subsequently blown out, or the fluid flow is turned off and they fall to deposit on the filter, or otherwise settle into the measurement region. Furthermore, particles with terminal settling velocities slightly higher than that of cut point particles may enter the collection container, but then fall slowly and tend to hover above the filter. Larger particles that fall through the container may impact these hovering particles and carry them to the filter. Hovering particles may also impact each other to form agglomerates that then deposit on the filter. Images of the samplers were examined to determine if particle aggolmerations were occuring in the collection container. The sampler filters had fewer agglomerates than the reference filters, indicating that particle agglomeration in the collection container is rare. Particle deposition on the walls was not evaluated quantitatively; however, visual inspection of the sampler walls did not reveal substantial deposits on the walls (to note—the particles tested here were large enough to be visible by the naked eye when present on the surface of the exterior of the sampler).

Embodiments of the subject matter disclosed herein include systems that employ a collection container that classifies a coarse aerosol into two fractions—one larger and one smaller than a specified cut size. In embodiments, the system may be configured to measure the size distribution of an aerosol. Embodiments of the system may employ multiple collection tubes that operate simultaneously, each with a different cut size. Other embodiments may employ a single collection tube operated in a way that steps through a series of cut sizes by sequentially adjusting its air flow and changing the filter between cut sizes. This spectrometer may be appropriate, for example, when the aerosol to be characterized is stable over the time necessary to step through the required flows. Embodiments of the system include a real-time particle sensor. For example, incorporating a photo-diode/detector into the collector for particle detection by light scattering could provide real-time analyses that may be useful for determining exposures in workplaces. Although most of the diseases associated with large particle exposure are chronic rather than acute, real-time measurements may be helpful to pinpoint where sources of exposure are occuring so that appropriate control actions can be taken.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A system for characterizing particles in an aerosol, based at least in part on an aerodynamic diameter of each of the particles, the aerodynamic diameter of a particular particle comprising a diameter of a sphere of unit density and having the same settling velocity as the particular particle, the system comprising:
   a collection container comprising:
   a first end having an opening;
   a second end, wherein the collection container is configured to be oriented such that an axis of symmetry extending from the first end to the second end is oriented substantially in a direction of gravitational settling of the particles; and
   a collection container wall extending between the first end and the second end, the collection container wall having an inner surface defining a collection chamber;
   a first flow device coupled to the second end and configured to provide a first fluid flow from the second end toward the first end, wherein the first fluid flow is configured such that particles having a first aerodynamic diameter settle into a measurement region of the collection tube;

a particle detector operatively coupled to the collection container, wherein the particle detector is configured to detect at least one particle within the measurement region of the collection chamber;

a housing, wherein at least a portion of the collection container is disposed within the housing, the housing comprising:

a first housing end having a cap disposed above, and spaced apart from, the first end of the collection container, the cap having an inlet aperture defined therein;

a second housing end; and a housing wall extending downward from the first housing end such that at least a portion of the housing wall is positioned external to, and spaced apart from, the collection container wall, thereby forming a gap between an outside surface of the collection container wall and an inside surface of the housing wall; and a second flow device operatively coupled to the housing and configured to provide a second fluid flow, within the gap, away from the first housing end, thereby creating a fluid stagnation region above the first end of the collection container, wherein the stagnation region comprises a region in which there is no net fluid flow along a direction parallel to the axis of symmetry.

2. The system of claim 1, further comprising a controller configured to control the first and second flow devices to create the fluid stagnation region.

3. The system of claim 1, wherein the particle detector includes a collection surface disposed at or near the second end of the collection container.

4. The system of claim 3, wherein the collection surface comprises a surface of a filter.

5. The system of claim 1, wherein the particle detector comprises a laser induced breakdown spectroscopy (LIBS) system, the LIBS system comprising:

a LIBS laser generator operatively coupled to the collection container and configured to provide a LIBS laser beam that produces a plasma within the collection chamber such that the produced plasma causes an optical emission when the at least one particle passes through the plasma; and a LIBS spectrometer operatively coupled to the collection container and configured to receive the optical emission and determine, based on the optical emission, a composition of the at least one particle.

6. The system of claim 5, the particle detector further comprising a trigger laser system, the trigger laser system comprising a trigger laser generator operatively coupled to the collection container and configured to provide a trigger laser beam within the collection chamber.

7. The system of claim 6, the trigger laser system further comprising a trigger photodetector operatively coupled to the collection container and configured to detect at least one of an interruption of the trigger laser beam by the at least one particle and Mie-scattered light produced when the at least one particle passes through the trigger laser beam.

8. The system of claim 7, the trigger laser system further configured to initiate, in response to detecting the at least one particle, detection by the LIBS laser generator and the LIBS spectrometer.

9. The system of claim 1, the particle detector further comprising a Mie scattering particle counting system, the Mie scattering particle counting assembly comprising:

a Mie scattering laser generator operatively coupled to the collection container and configured to provide a Mie scattering laser sheet in the collection chamber; and a Mie scattering photodetector operatively coupled to the collection container and configured to (1) produce a signal in response to detecting light scattered off of the at least one particle when the at least one particle intersects the Mie scattering laser sheet, (2) determine whether the signal exceeds a threshold, and (3) register a count if the signal exceeds the threshold.

10. The system of claim 1, wherein the controller is configured to:

receive a first user input specifying the first aerodynamic diameter;

adjust, in response to receiving the first user input, at least one of the first and second flow devices to configure the system to collect particles having the first aerodynamic diameter;

receive a second user input specifying a second aerodynamic diameter; and adjust, in response to receiving the second user input, at least one of the first and second flow devices to configure the system to collect particles having the second aerodynamic diameter.

11. The system of claim 1, wherein the first aerodynamic diameter is at least ten microns.

12. The system of claim 1, wherein the first aerodynamic diameter is no less than ten microns and no greater than one hundred microns.

* * * * *